(12) United States Patent
Mitsuno et al.

(10) Patent No.: US 9,322,816 B2
(45) Date of Patent: Apr. 26, 2016

(54) GAS SENSOR CONTROL APPARATUS

(71) Applicant: NGK SPARK PLUG CO., LTD., Nagoya-shi, Aichi (JP)

(72) Inventors: Junichiro Mitsuno, Kitanagoya (JP); Tomonori Uemura, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 461 days.

(21) Appl. No.: 13/767,448

(22) Filed: Feb. 14, 2013

(65) Prior Publication Data

US 2013/0205870 A1    Aug. 15, 2013

(30) Foreign Application Priority Data

Feb. 15, 2012  (JP) .................................. 2012-030966
Feb. 27, 2012  (JP) .................................. 2012-039668
Aug. 24, 2012  (JP) .................................. 2012-185892

(51) Int. Cl.
*G01N 33/00*   (2006.01)
*G01N 27/406*  (2006.01)

(52) U.S. Cl.
CPC ........ *G01N 33/0073* (2013.01); *G01N 27/4067* (2013.01)

(58) Field of Classification Search
CPC ....................... G01N 27/4067; G01N 33/0073
See application file for complete search history.

(56) References Cited

U.S. PATENT DOCUMENTS

| | | | | |
|---|---|---|---|---|
| 6,384,386 B2* | 5/2002 | Hashimoto | .......... | G01N 27/122 123/697 |
| 6,720,534 B2* | 4/2004 | Hada | .................. | G01N 27/4067 204/425 |
| 6,870,142 B2 | 3/2005 | Hada et al. | | |
| 6,921,883 B2* | 7/2005 | Kato | .................. | G01N 27/4067 123/179.1 |
| 8,635,900 B2* | 1/2014 | Ante | .................. | F02D 41/1466 73/23.33 |
| 2002/0179443 A1 | 12/2002 | Hada et al. | | |

FOREIGN PATENT DOCUMENTS

| | | |
|---|---|---|
| JP | 2006-113081 A | 4/2006 |
| JP | 4241737 B2 | 3/2009 |

* cited by examiner

*Primary Examiner* — Daniel S Larkin
(74) *Attorney, Agent, or Firm* — Sughrue Mion, PLLC

(57) ABSTRACT

A gas sensor control apparatus (1) for controlling a gas sensor (2) includes a change amount detection means (40); an element resistance detection means for detecting the element resistance Rpvs of a sensor element section (3) on the basis of the response change amount ΔVs; a heater energization control section for on-off controlling the supply of electric current to a heater section (4) by pluses PS having a fixed period T; and an instruction signal output section for instructing the change amount detection section (40) to detect the response change amount ΔVs at a third timing t3 which comes after elapse of a predetermined wait time TW from a second timing t2 (heater energization off) which changes in accordance with the pulse width PSW.

17 Claims, 21 Drawing Sheets

GAS SENSOR CONTROL APPARATUS

BACKGROUND OF THE INVENTION

1. Field of the Invention

The present invention relates to a gas sensor control apparatus for controlling a gas sensor which detects the concentration of a gas.

2. Description of the Related Art

Conventionally, a gas sensor has been used which is mounted on a vehicle and is attached to an exhaust pipe of an internal combustion engine, and which detects the concentration of a specific gas contained in an exhaust gas, for the purpose of, for example, controlling an air-fuel ratio. Known examples of such a gas sensor include an oxygen sensor for detecting the concentration of oxygen and an NOx sensor for detecting the concentration of nitrogen oxide (NOx). Such a gas sensor often uses a solid electrolyte member mainly made of zirconia (zirconium oxide) in a sensor element section. Such a solid electrolyte member becomes active when heated to a high temperature (about 600° C. or higher), and exhibits excellent oxygen ion conductivity. In view of this, in a gas sensor in which a solid electrolyte member is used in the sensor element section, a heater section for heating the sensor element section is provided so as to heat the sensor element section to an activation temperature at which the sensor element section becomes active. In order to maintain the sensor element section at a proper activation temperature, the element resistance having a certain relation with the element temperature of the sensor element section is detected, and the supply of electric current to the heater section is feedback-controlled such that the element resistance coincides with a target resistance.

[Patent Document 1] Japanese Patent Application Laid-Open (kokai) No 2006-113081

3. Problems to be Solved by the Invention:

Incidentally, in order to perform the above-mentioned heater energization under feedback control in such a gas sensor, it is necessary to detect the element resistance of the sensor element section regularly, while controlling the energization of the heater section. One known method of detecting the element resistance of the sensor element section is temporarily changing the voltage between the electrodes of the sensor element section or the current flowing between the electrodes, detecting the change in voltage or current in response to the temporal change (the magnitude of the change will be referred to as a response change amount), and detecting the element resistance from the response change amount. Meanwhile, since on-off control (PWM control) is performed through use of pulses in order to control the energization of the heater section, switching noise may be generated at the leading edge and trailing edge of each pulse; namely, at timings at which the state of heater energization is switched from the OFF state to the ON state and switched from the ON state to the OFF state. Accordingly, if the timing of switching the heater energization state overlaps with a period during which the response change amount is detected by the above-described method, the switching noise affects the detected response change amount, and in some cases the element resistance cannot be detected accurately.

In order to solve such a problem, for example, Patent Document 1 discloses a heater control apparatus for a gas concentration sensor which is configured such that when the element resistance detection period and the timing of on/off switching of heater energization overlap each other, the detection period or the switching timing is forcedly shifted.

However, such a control apparatus must always monitor the detection period and the switching timing and determine whether or not they overlap each other. When the detection period and the switching timing are expected to overlap each other, the control apparatus must adjust the detection period or the switching timing so as to prevent the occurrence of such overlap. Therefore, control tends to become complex, and there is a need for simpler, more reliable measures against such overlap between the detection period and the switching timing. In particular, there is a need for measures against irregular overlap at a timing which changes with a change in pulse width caused by feedback control, the timing being one of timings corresponding to the leading edge and trailing edge of each pulse.

SUMMARY OF THE INVENTION

The present invention has been accomplished in view of the above-mentioned problems, and provides a gas sensor control apparatus which can accurately detect the resistance of a sensor element by suppressing the influence of switching noise generated as a result of switching at a timing which changes with a change in pulse width, the timing being one of the timing at which the state of heater energization is switched from the OFF state to the ON state and the timing at which the state of heater energization is switched from the ON state to the OFF state.

The above objects have been achieved, in accordance with a first aspect (1) of the invention, by providing a gas sensor control apparatus for controlling a gas sensor which includes a sensor element section made of a solid electrolyte member and detecting the concentration of a gas, and a heater section for heating the sensor element section, comprising change amount detection means for causing a temporary change in voltage between electrodes of the sensor element section or current flowing between the electrodes and for detecting, as a response change amount, a change in the voltage or the current produced in response to the temporary change; element resistance detection means for detecting an element resistance of the sensor element section on the basis of the response change amount; instruction signal output means for outputting an instruction signal for instructing the change amount detection means to detect the response change amount; and heater energization control means for on-off controlling the state of supply of electric current to the heater section through use of pulses having a fixed period, wherein when, of an energization ON edge timing of the respective pulses at which the state of supply of electric current to the heater section is switched from an OFF state to an ON state and an energization OFF edge timing of the respective pulses at which the state of supply of electric current to the heater section is switched from the ON state to the OFF state, a timing which occurs at fixed intervals corresponding to the fixed period is defined as a first timing, and a timing which changes depending on a pulse width of the pulses is defined as a second timing, the instruction signal output means outputs the instruction signal at a third timing which comes after elapse of a predetermined wait time from the second timing.

The gas sensor control apparatus (1) includes an instruction signal output means which outputs, at the above-described third timing, an instruction signal for instructing the change amount detection means to detect the response change amount.

By virtue of this configuration, a predetermined wait time is provided between the second timing and the third timing, and the response change amount is detected in response to the instruction at the third timing. Thus, the switching of the energization state of the heater section at the second timing does not overlap with the timing at which the response change amount is detected. Therefore, switching noise generated as a result of at least the switching of the heater energization state at the timing which changes with the pulse width, is prevented from affecting the detection of the response change amount (and accordingly, detection of the element resistance). Accordingly, the element resistance can be detected properly (i.e., without being affected by switching noise).

In addition, since the required operation is outputting the instruction signal at the third timing which comes after elapse of a predetermined wait time from the second timing, complicated control for timing adjustment is not required.

Notably, preferably, the length of the wait time from the second timing to the third timing is determined such that it is long enough to prevent the switching noise generated at the second timing from affecting the detection of the response change amount.

Also, each of the response change amount detected by the change amount detection means and the temporary change which is produced between the electrodes of the sensor element section so as to obtain the response change amount may be a voltage change or a current change, which can be selected by properly changing the configuration of the change amount detection means.

Examples of the gas sensor of the present invention includes a full range oxygen sensor for linearly detecting the concentration of oxygen contained in a gas to be measured, an oxygen sensor for detecting the concentration (lean/rich) of oxygen, and an NOx sensor for detecting the concentration of nitrogen oxide (NOx).

In a preferred embodiment (2) of the above-described gas sensor control apparatus (1), the heater energization control means feedback-controls the supply of electric current to the heater section such that the element resistance detected by the element resistance detection means becomes equal to a target resistance.

In the gas sensor control apparatus (2), since the supply of electric current to the heater section is feedback-controlled by the heater energization control means, the sensor element section can be maintained at a proper activation temperature, whereby the gas concentration can be detected properly.

In another preferred embodiment (3) of the above-described gas sensor control apparatus (1), the instruction signal output means outputs the instruction signal every n-th period, where n is an integer equal to or greater than 2.

In the gas sensor control apparatus (3), at every n-th period of the pulses that has elapsed (e.g., at every 10-th period of the elapsed pulses); in other words, every time the period of the pulses occurs n times (e.g., 10 periods), the instruction signal is output so as to detect the response change amount. By virtue of this configuration, the response change amount and the element resistance based thereon can be detected regularly. In addition, the interval of the detection of the element resistance can be made longer than (n times) the period of the pulses for controlling the supply of electric current to the heater section. Therefore, when the energization of the heater section is feedback-controlled, the control can be performed stably by suppressing oscillation or the like.

In yet another preferred embodiment (4) of the above-described gas sensor control apparatus (1) to (3), a time between a commencement of the output of the instruction signal and a completion of the detection of the response change amount by the change amount detection means is defined as a detection delay time; periods each continuing from the first timing to the second timing which comes next are defined as 1-2 periods; periods each continuing from the second timing to the first timing which comes next are defined as 2-1 periods; of the 2-1 periods, those which include the third timing at which the instruction signal is output are defined as an output 2-1 period; of the 1-2 periods, those immediately before the output 2-1 periods are defined as a pre-output 1-2 period; and the heater energization control means includes maximum value restriction means for restricting the length of the pre-output 1-2 period to a maximum value or less which is previously determined within a range within which the output 2-1 period becomes longer than the sum of the wait time and the detection delay time.

In the gas sensor control apparatus (4), the length of the pre-output 1-2 period is restricted to the maximum value or less. Notably, this maximum value is determined to fall within a range within which the output 2-1 period becomes longer than the sum of the wait time and the detection delay time. Therefore, even in the case where the interval between the second timing and the first timing which comes next is shortened by changing the pulse width for energization control of the heater section, when the detection of the response change amount is performed, the length of the pre-output 1-2 period is restricted to the maximum value or less. Accordingly, the period in which the response change amount is detected does not overlap with the switching of the heater energization state at the first timing. By virtue of this configuration, not only the switching noise generated as a result of switching of the heater energization state at the second timing, which changes in accordance with the pulse width, but also the switching noise generated as a result of switching of the heater energization state at the first timing, which comes at fixed intervals corresponding to the period of the pluses is reliably prevented from affecting the detection of the response change amount (namely, detection of the element resistance). Therefore, the element resistance can be detected more properly.

In yet another preferred embodiment (5) of the above-described gas sensor control apparatus (4), the maximum value restriction means restricts the length of all the 1-2 periods $T_{1-2}$, including the pre-output 1-2 period, to the maximum value or less.

In the gas sensor control apparatus (5), the length of all the 1-2 periods is restricted to the maximum value or less. By virtue of this configuration, the same control can be performed in both the periods in which the instruction signal is output and the remaining periods. Therefore, the control becomes simple.

In yet another preferred embodiment (6) of the above-described gas sensor control apparatus (4), preferably, the heater energization control means includes the minimum value restriction means for restricting the length of the pre-output 1-2 periods to a predetermined minimum value or greater, where the minimum value is greater than zero.

In the gas sensor control apparatus (6), the length of the pre-output 1-2 period is restricted to the minimum value (greater than zero) or greater. By virtue of this configuration, even in the case where the interval between the first timing and the second timing which comes next is shortened by changing the pulse width for energization control of the heater section, when the detection of the response change amount is performed, the length of the pre-output 1-2 period is restricted to the minimum value (greater than zero) or greater. Accordingly, the case does not exist where the length of the pre-output 1-2 period is zero; i.e., the case where the first timing and the second timing are not present. Namely, the first timing and the second timing are present without fail. Therefore, the third timing subsequent to the second timing can be secured, and the timing for detecting the response change amount is not missed. Thus, the element resistance can be detected regularly without fail.

In yet another preferred embodiment (7) of the above-described gas sensor control apparatus (6), the minimum value restriction means restricts the length of all the 1-2 periods, including the pre-output 1-2 period, to the minimum value or greater.

In the gas sensor control apparatus (7), the length of all the 1-2 periods is restricted to the minimum value or greater. By virtue of this configuration, the same control can be performed in both the periods in which the instruction signal is output and the remaining periods. Therefore, the control becomes simple.

In yet another preferred embodiment (8) of the above-described gas sensor control apparatus (6), the first timing is the energization ON edge timing, and the second timing is the energization OFF edge timing.

Incidentally, in the case where the heater section is controlled such that electric current is supplied to the heater section during the 2-1 periods and the supply of electric current to the heater section is stopped during the 1-2 periods, the above-mentioned maximum value for the pre-output 1-2 period becomes the maximum value for the periods during which the supply of electric current to the heater section is stopped. In contrast, in this case, the minimum value (length) of the periods during which electric current is supplied to the heater section is controlled such that it becomes longer the sum of the wait time and the detection delay time due to restriction by the maximum value (length) of the pre-output 1-2 period. Namely, even in the case where the supply of electric current to the heater section is unnecessary or the supply of electric current to the heater section is required only for a very short period of time, the period during which electric current is supplied to the heater section cannot be shortened sufficiently.

In contrast, in the present gas sensor control apparatus, the state of supply of electric current to the heater section is switched from the OFF state to the ON state at the first timing, and is switched from the ON state to the OFF state at the second timing. Namely, electric current is supplied to the heater section during the 1-2 periods, and the supply of electric current to the heater section is stopped during the 2-1 periods. Accordingly, the minimum value (length) of the pre-output 1-2 period becomes the minimum value (length) of the periods during which electric current is supplied to the heater section.

No limitation is imposed on the minimum value (length) of the pre-output 1-2 period unlike the maximum value of the pre-output 1-2 period (however, the minimum value is greater than 0). Therefore, in the case where the supply of electric current to the heater section is unnecessary or the supply of electric current to the heater section is required only for a very short period of time, the length of the periods during which electric current is supplied to the heater section can be shortened to the minimum length of the pre-output 1-2 period. Accordingly, it is possible to properly control the energization of the heater section while suppressing the consumption of electric power by the heater section.

In yet another preferred embodiment (9), the above-described gas sensor control apparatus (1) comprises data transmission means for transmitting data to an external device; and prevention means for preventing use of the response change amount and the element resistance obtained therefrom, the response change amount being affected by the transmission of data due to overlap between the transmission period of the data and at least a portion of the detection period of the response change amount subsequent to the output of the instruction signal at the third timing.

The gas sensor control apparatus transmits data representing the measured gas concentration or the like to an external device such as an ECU. At that time, the consumed current increases due to the data transmission, and the power supply voltage of the control circuit may fluctuate. Therefore, in the case where at least a portion of the period of detection of the response change amount subsequent to the output of the instruction signal at the third timing overlaps with the data transmission period, the value of the response change amount detected by the change amount detection means and the value of the element resistance detected on the basis of the response change amount are affected. Accordingly, there is a possibility that a proper value of the element resistance cannot be obtained.

In contrast, since the present gas sensor control apparatus includes the prevention means, it is possible to prevent use of the response change amount or the element resistance obtained from the response change amount, the response change amount being affected by the transmission of data because of overlap between the period during which the response change amount is detected and the period during which data are transmitted to the external device.

In yet another preferred embodiment (10) of the above-described gas sensor control apparatus (9), the prevention means includes pre-output transmission determination means for determining, prior to the output of the instruction signal at the third timing, whether or not the transmission of the data by the data transmission means is being performed at a pre-output determination timing within the period to which the third timing belongs, the pre-output determination timing coming before the third timing; and output stopping means for stopping the output of the instruction signal at the third timing when the transmission of the data is determined to be being performed.

In the gas sensor control apparatus (10), the prevention means includes the pre-output transmission determination means which determines, prior to the output of the instruction signal at the third timing, whether or not the transmission of the data is being performed, and output stopping means which stops the output of the instruction signal at the third timing.

By virtue of this configuration, the response change amount and the element resistance are prevented from assuming values affected by the transmission of data, and only a proper value of the element resistance is used.

In yet another preferred embodiment (11) of the above-described gas sensor control apparatus (9), the prevention means includes intra-period transmission determination means for determining, at the first timing within the period to which the third timing belongs, whether or not the transmission of the data by the data transmission means is performed within the period; and output stopping means for stopping the output of the instruction signal at the third timing when the transmission of the data is determined to be performed.

In the gas sensor control apparatus (11), the prevention means includes the intra-period transmission determination means and the output stopping means.

By virtue of this configuration, the response change amount and the element resistance are prevented from assuming values affected by the transmission of data, and only a proper value of the element resistance is used.

In yet another preferred embodiment (12) of the above-described gas sensor control apparatus (10) or (11), the instruction signal output means outputs the instruction signal every n-th period, where n is an integer equal to or greater than 2; and the prevention means includes period postponing output means, operable when the output of the instruction signal at the third timing is stopped, for outputting the instruction signal at the third timing in a period subsequent to the period in which the output of the instruction signal was stopped.

In the gas sensor control apparatus (12), the instruction signal output means outputs the instruction signal every time the period of the pulses occurs n times (e.g., 10 times). In the case where the output of the instruction signal at the third timing is stopped, the instruction signal is output at the third timing in the period subsequent to the period in which the output of the instruction signal was stopped.

By virtue of this configuration, even when the output of the instruction signal at the third timing is stopped once, it is possible to output the instruction signal in the next period so as to obtain a proper response change amount, whereby a proper element resistance can be detected regularly.

In yet another preferred embodiment (13) of the above-described gas sensor control apparatus (10), the instruction signal output means outputs the instruction signal every n-th period, where n is an integer equal to or greater than 2; and the prevention means includes timing postponing output means, operable when the output of the instruction signal at the third timing is stopped, for outputting the instruction signal at a fourth timing within the period in which the output of the instruction signal was stopped, the fourth timing coming after the third timing.

In the gas sensor control apparatus (10), the instruction signal output means outputs the instruction signal every time the period of the pulses comes n times. In the case where the output of the instruction signal at the third timing is stopped, the instruction signal is output at the fourth timing after the third timing in the period in which the output of the instruction signal was stopped.

By virtue of this configuration, even when the output of the instruction signal at the third timing is stopped once, it is possible to output the instruction signal at the fourth timing subsequent to the third timing so as to obtain the response change amount, whereby the element resistance can be detected regularly.

In the above-described gas sensor control apparatus (13), the prevention means includes postponing transmission determination means for determining whether or not the transmission of data by the data transmission means is being performed at a postponing determination timing between the pre-output determination timing and the fourth timing; and output permission means for permitting the output of the instruction signal at the fourth timing by the timing postponing output means when it is determined that the transmission of data is not being performed.

In the gas sensor control apparatus (13), a determination is made as to whether or not the data transmission is being performed at the postponing determination timing, and then the output of the instruction signal at the fourth timing is permitted. Therefore, a proper response change amount can be obtained, whereby a proper element resistance can be detected regularly.

In yet another preferred embodiment (14) of the above-described gas sensor control apparatus (9), preferably, the prevention means includes pre-detection transmission determination means for determining whether or not the transmission of the data by the data transmission means is being performed at a pre-detection determination timing within the period to which the third timing belongs, the pre-detection determination timing coming before the detection period; and use prohibition means for preventing use of the response change amount detected in the detection period or the element resistance detected from the response change amount when the transmission of the data is determined to be being performed.

In the gas sensor control apparatus (14), the pre-detection transmission determination means is provided, and, in the case where the transmission of data is being performed at the pre-detection determination timing before the detection period, the response change amount detected in the detection period or the element resistance detected therefrom is not used.

By virtue of this configuration, the response change amount or the element resistance affected by the transmission of data is not used, and only a proper value of the element resistance is used.

In yet another preferred embodiment (15) of the above-described gas sensor control apparatus (14), preferably, the instruction signal output means outputs the instruction signal every n-th period, where n is an integer equal to or greater than 2; and the prevention means includes re-output means, operable when the pre-detection transmission determination means determines that the transmission of the data is being performed, for causing the instruction signal output means to output the instruction signal again in a period subsequent to the period in which the instruction signal was output.

In the gas sensor control apparatus (15), the instruction signal output means outputs the instruction signal every time the period of the pulses occurs n times. In the case where the pre-detection transmission determination means determines that the transmission of data is being performed, the instruction signal output means is caused to output the instruction signal again in the period subsequent to the period in which the instruction signal was output.

By virtue of this configuration, the response change amount or the element resistance obtained when the detection period and the data transmission period overlap each other are prevented from being used, and the instruction signal is output again in the next period in order to obtain the response change amount, whereby the element resistance can be detected. Thus, the element resistance can be detected substantially regularly.

In yet another preferred embodiment (16) the above-described gas sensor control apparatus (9), the prevention means includes overlap determination means for determining whether or not at least a portion of the detection period has actually overlapped with the transmission period of transmission of the data transmitted by the data transmission means; and use prohibition means for preventing use of the response change amount detected in the detection period or the element resistance detected from the response change amount when at least a portion of the detection period is determined to have overlapped with the transmission period.

In the gas sensor control apparatus (16), overlap determination means is provided which determines whether or not at least a portion of the detection period has actually overlapped with the data transmission period. In the case where a determination is made that at least a portion of the detection period has actually overlapped with the data transmission period, the response change amount detected in the overlapping detection period or the element resistance obtained therefrom are prevented from being used, Thus, the response change amount or the element resistance affected by the transmission of data is not used, whereby only a proper value of the element resistance is used.

In yet another preferred embodiment (17) of the above-described gas sensor control apparatus (16), preferably, the instruction signal output means outputs the instruction signal every n-th period, where n is an integer equal to or greater than 2; and the prevention means includes re-output means, operable when the overlap determination means determines that at least a portion of the detection period has overlapped with the transmission period, for causing the instruction signal output means to output the instruction signal again in a period subsequent to the period in which the instruction signal was output.

In the gas sensor control apparatus (17), the instruction signal output means outputs the instruction signal every time the period of the pulses occurs n times. Meanwhile, in the case where the overlap determination means determines that overlap has occurred, the instruction signal output means is caused to output the instruction signal again in the period subsequent to the period in which the instruction signal was output.

By virtue of this configuration, the response change amount obtained when the detection period overlapped with the data transmission period or the element resistance obtained from the response change amount is prevented from being used, and the instruction signal is output again in the next period, whereby a proper response change amount is obtained. Therefore, a proper element resistance can be detected substantially regularly.

DESCRIPTION OF REFERENCE NUMERALS AND SYMBOLS

Figure 1:
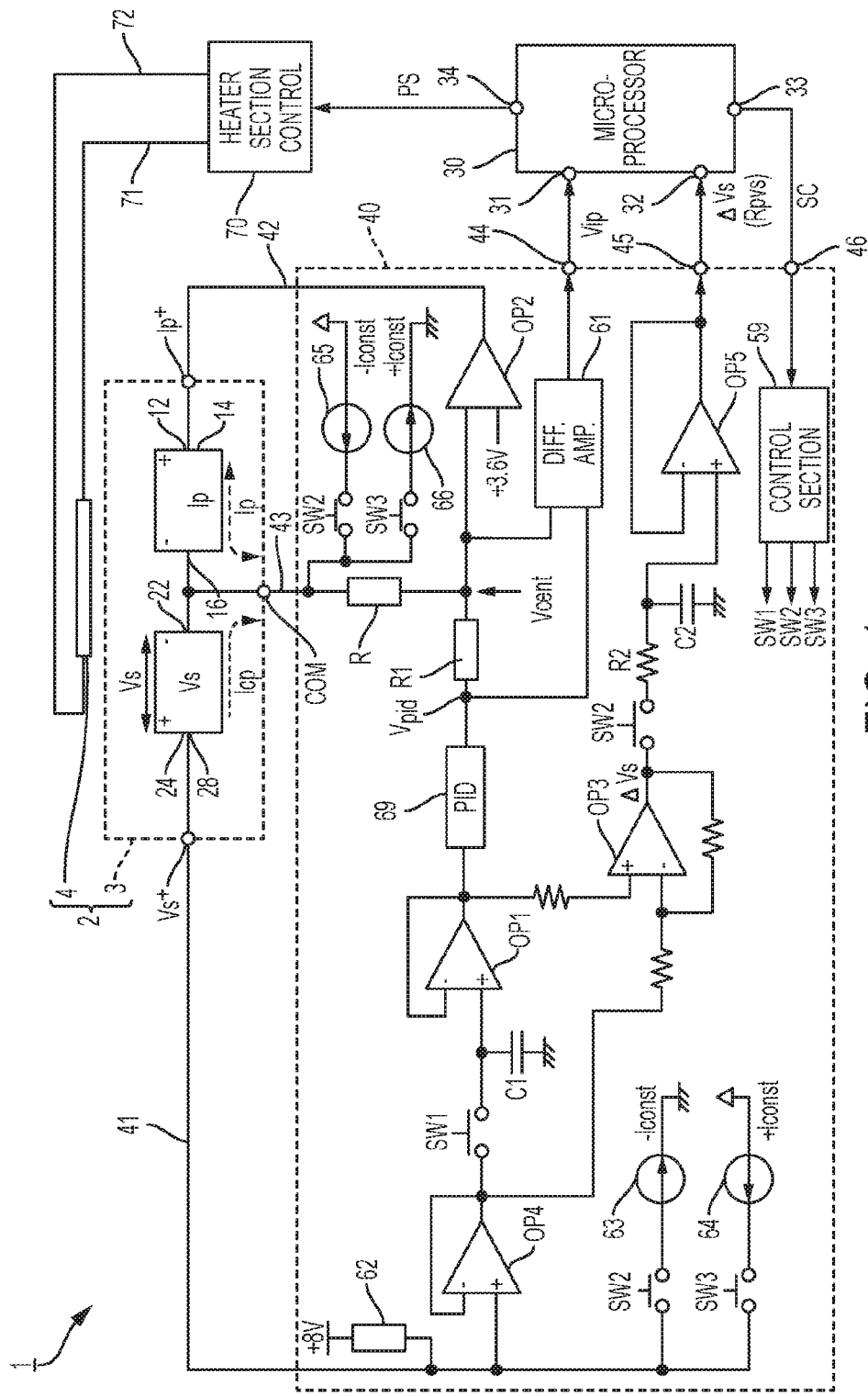
FIG. 1 is an explanatory diagram schematically showing the configuration of a gas sensor control apparatus according to an embodiment of the invention.

Reference numerals and symbols used to identify various features in the drawings include the following.
1, 1A, 1B, 1C, 1D, 1E: gas sensor control apparatus
2: gas sensor
3: sensor element section
4: heater section
14: pump cell
24: electromotive force cell
22, 28: electrode (of the electromotive force cell)
Vs+, Ip+, COM: terminal (of the sensor element section)
Vs: electromotive force cell voltage
$\Delta$Vs: voltage change amount (response change amount)
Rpvs: element resistance of (the electromotive force cell)
30: microprocessor
34: PWM output port (heater energization control means)
40: sensor element section control circuit (change amount detection means)
70: heater section control circuit (heater energization means)
35: CAN protocol controller (data transmission means)
80: CAN transceiver (data transmission means)
100: ECU (external device)
T: period
PS: PWM pulse (pulse)
PSW: pulse width
ton: energization ON edge timing
toff: energization OFF edge timing
t1: first timing
t2: second timing
t3: third timing
TW: wait time
SC: instruction command (instruction signal)
RT: target resistance
TD: detection delay time
TK: detection operation period (detection period)
$T_{1-2}$: 1-2 period
$T_{2-1}$: 2-1 period
$TB_{1-2}$: pre-output 1-2 period
$TO_{2-1}$: output 2-1 period
$TB_{1-2max}$: maximum value of (the pre-output 1-2 periods)
$TB_{1-2min}$: minimum value of (the pre-output 1-2 periods)
S4, S71 to S77: heater energization control means
S73 to S74: maximum value control means
S75 to S76: minimum value control means
S25 to S28: element resistance detection means
S32 to S37: instruction signal output means
S131 to S134, S231 to S232, S41 to S43, S331 to S334, S431 to S434, S421, S531 to S536: prevention means
S131, S231: pre-output transmission determination means
S131, S231, S331: output stopping means
S132, S133, S134, S332, S333, S334: period postponing output means
S231, S232: timing postponing output means
S41, S42, S43: intra-period transmission determination means
S431: pre-detection transmission determination means
S432, S433, S434, S421, S534, S535: use prohibition means
S432, S433, S434, S534, S535, S536: re-output means
S531 to S533: overlap determination means

DETAILED DESCRIPTION OF THE PREFERRED EMBODIMENTS

An embodiment of the present invention will now be described with reference to the drawings. However, the present invention should not be construed as being limited thereto.

FIG. 1 is a diagram schematically showing the configuration of a gas sensor control apparatus 1 according to the present embodiment. The gas sensor control apparatus 1 includes a gas sensor 2, a microprocessor 30, a sensor element section control circuit 40, and a heater section control circuit 70.

Of these, the gas sensor 2 is an air-fuel-ratio sensor (wide-range oxygen sensor) which is attached to the exhaust pipe of the internal combustion engine of an unillustrated vehicle, linearly detects the oxygen concentration (air-fuel ratio) of exhaust gas, and is used so as to perform feedback control of air-fuel ratio for the internal combustion engine. The gas sensor 2 includes a sensor element section 3 for detecting the oxygen concentration, and a heater section 4 for heating the sensor element section 3.

The sensor element section 3 has a known structure in which a pump cell 14 and an electromotive force cell 24 are stacked via a spacer constituting a hollow measurement chamber (not shown) into which exhaust gas can be introduced. An electrode located on one side of the electromotive force cell 24 opposite the measurement chamber is covered by a protective layer (not shown). Each of the pump cell 14 and the electromotive force cell 24 includes, as a substrate, a platelike, oxygen-ion-conductive solid electrolyte member mainly made of zirconia, and porous platinum electrodes 12, 16 and 22, 28 formed on opposite sides of the substrate. The electrode 16 at one end of the pump cell 14 and the electrode 22 at one end of the electromotive force cell 24 are electrically connected to each other and are connected to a terminal COM of the sensor element section 3. The electrode 12 at the other end of the pump cell 14 is connected to a terminal Ip+ of the sensor element section 3, and the electrode 28 at the other end of the electromotive force cell 24 is connected to a terminal Vs+ of the sensor element section 3.

The sensor element section control circuit 40 is mainly constituted by an ASIC (Application-Specific Integrated Circuit), and is connected to the terminals Vs+, Ip+, COM of the sensor element section 3 via connection paths 41, 42, 43 (specifically, wiring lines on the circuit and lead wires). While supplying a very small current Icp to the electromotive force cell 24 of the sensor element section 3, the sensor element section control circuit 40 controls the pump cell current Ip flowing through the pump cell 14. Particularly, that the electromotive force cell voltage Vs becomes 450 mV, to thereby pump out oxygen contained in the exhaust gas introduced into the measurement chamber or pump oxygen into the measurement chamber. Since the magnitude and flow direction of the pump cell current Ip flowing through the pump cell 14 change depending on the oxygen concentration (air-fuel ratio) of the exhaust gas, the concentration of oxygen contained in the exhaust gas can be calculated on the basis of the pump cell current Ip.

In the sensor element section control circuit 40, the magnitude of the pump cell current Ip is converted to a voltage signal, which is output from a gas detection signal output terminal 44 as a gas detection signal Vip (to be described later). Also, in addition to the gas detection signal Vip, the sensor element section control circuit 40 detects a voltage change amount ΔVs (described below). The voltage change amount ΔVs changes in accordance with the element resistance Rpvs of the electromotive force cell 24 of the sensor element section 3, and is output from a voltage change amount output terminal 45. The microprocessor 30 receives the gas detection signal Vip and the voltage change amount ΔVs via A/D input ports 31, 32.

The heater section control circuit 70 is connected to the heater section 4 of the gas sensor 2 via two lead wires 71, 72, and is connected to a PWM output port 34 of the microprocessor 30. The heater section control circuit 70 supplies electric current to the heater section 4, through PWM control, in accordance with PWM pulses PS output from the PWM output port 34. The heater section 4 is united with the sensor element section 3. Through heating by the heater section 4, the pump cell 14 and the electromotive force cell 24 of the sensor element section 3 are activated, whereby detection of the oxygen concentration becomes possible.

The heater section control circuit 70 supplies electric current to the heater section 4 when a signal containing the PWM pulses PS output from the PWM output port 34 of the microprocessor 30 is at an H level. Also, the heater section control circuit 70 stops the supply of electric current to the heater section 4 when the signal containing the PWM pulses PS is at an L level.

Next, operation of the sensor element section control circuit 40 for detecting the oxygen concentration through use of the sensor element section 3 will be described.

The terminal COM of the sensor element section 3 is connected to a Vcent point of the sensor element section control circuit 40 via the connection path 43 and a resistor R of the sensor element section control circuit 40. The terminal Ip+ is connected to the output terminal of a second operational amplifier OP2 of the sensor element section control circuit 40 via the connection path 42. The terminal Vs+ is connected to the noninverting input terminal+ of a fourth operational amplifier OP4 of the sensor element section control circuit 40 via the connection path 41. The terminal Vs+ is also connected to a constant current source circuit 62 of the sensor element section control circuit 40. The constant current source circuit 62 includes a constant current source and a resistor connected in series thereto, and supplies the above-mentioned very small current Icp to the electromotive force cell 24.

The sensor element section control circuit 40 is composed of first through fifth operational amplifiers OP1-OP5, one first switch SW1, three second switches SW2, two third switches SW3, a PID control circuit 69, a differential amplification circuit 61, current sources 63, 64, 65, 66, a control section 59, etc., as well as the above-mentioned resistor R and constant current source circuit 62. The constant current source circuit 62, the electromotive force cell 24, and the resistor R are connected in this order through the connection path 41, 43 to thereby form a current path through which the very small current Icp is caused to flow.

When the oxygen concentration is measured, the first switch SW1 is brought into the ON state by the control section 59. As a result, the potential at the terminal Vs+ of the sensor element section 3 is input to the PID control circuit 69 via the connection path 41 and the fourth operational amplifier OP4 and the first operational amplifier OP1, which form a voltage follower circuit. The control section 59 is a logic circuit formed within the ASIC, which constitutes the sensor element section control circuit 40. The control section 59 is connected to a serial transmission port 33 of the microprocessor 30 via a command reception port 46 of the sensor element section control circuit 40. In response to instructions from the microprocessor 30, the control section 59 controls the ON/OFF states of the first through third switches SW1-SW3 and performs other controls.

One input terminal of the second operational amplifier OP2 is connected to the Vcent point, and a reference voltage (+3.6 V) is applied to the other input terminal of the second operational amplifier OP2. As described above, the output terminal of the second operational amplifier OP2 is connected to the terminal Ip+ of the sensor element section 3 via the connection path 42.

The PID control circuit 69 controls the magnitude of the pump cell current Ip by means of PID control (proportional-integral-derivative control) such that a voltage difference of 450 mV is produced between the potential at the Vcent point and the potential at the terminal Vs+ of the sensor element section 3 which is input via the fourth operational amplifier OP4 and the first operational amplifier OP1. Specifically, the PID control circuit 69 calculates, through PID computation, the difference between a target control voltage (450 mV) and the electromotive force cell voltage Vs between the electrodes 28, 22 of the electromotive force cell 24, and feeds the difference back to the second operational amplifier OP2. Thus, the second operational amplifier OP2 supplies the pump cell current Ip to the pump cell 14.

Moreover, the sensor element section control circuit 40 includes a detection resistor R1, which detects the magnitude of the pump cell current Ip, and converts it to a voltage signal. The voltage generated across the detection resistor R1 (the difference between potentials Vcent and Vpid) is differentially amplified by the differential amplification circuit 61, and is output from the gas detection signal output terminal 44 as the gas detection signal Vip.

The microprocessor 30 receives the gas detection signal Vip through the A/D input port 31, and converts it to a digital value. The microprocessor 30 then calculates an oxygen concentration corresponding to the gas detection signal Vip on the basis of a map or a calculation equation held therein.

Next, the operation of the sensor element section control circuit 40 for detecting a voltage change amount ΔVs will be described, which changes with the element resistance Rpvs of the electromotive force cell 24 of the sensor element section 3.

In the sensor element section control circuit 40, the first operational amplifier OP1 forms a sample hold circuit in cooperation with the first switch SW1 and a capacitor C1. When the operation of detecting the voltage change amount ΔVs is performed, the first switch SW1 is switched from the ON state to the OFF state by the control section 59. As a result, the sample hold circuit holds the potential at the terminal Vs+ of the sensor element section 3 immediately before performing the operation of detecting the voltage change amount ΔVs. Therefore, during a period during which the operation of detecting the voltage change amount ΔVs is being performed, the potential at the terminal Vs+ before performing the operation of detecting the voltage change amount ΔVs (the voltage held by the first operational amplifier OP1) is input to the PID control circuit 69, and a gas detection signal Vip corresponding to the held voltage is output from the gas detection signal output terminal 44.

Also, the control section 59 switches the second switches SW2 from the OFF state to the ON state after having brought the first switch SW1 into the OFF state. At this time, the third switches SW3 remain in the OFF state. It is only during a period during which the second switches SW2 are in the ON state that a current path is temporarily formed starting from the current source 65 and extending through one second switch SW2, the connection path 43, the terminal COM (the electrode 22), the electromotive force cell 24, the terminal Vs+ (the electrode 28), the connection path 41, another second switch SW2, and the current source 63 in this order. In this manner, the constant current −Iconst flows through the electromotive force cell 24.

The third operational amplifier OP3, which forms a differential amplification circuit, outputs a voltage corresponding to the difference between the voltage held by the first operational amplifier OP1 (the potential at the terminal Vs+ at the time immediately before the present time) and the potential at the terminal Vs+ generated as a result of the flow of the constant current −Iconst through the electromotive force cell 24 (the output of the fourth operational amplifier OP4). This voltage is the voltage change amount ΔVs.

The voltage change amount ΔVs output from the third operational amplifier OP3 is input to a sample and hold circuit formed by the fifth operational amplifier OP5 in cooperation with the corresponding second switch SW2, a resistor R2, and a capacitor C2. In this sample and hold circuit, the voltage change amount ΔVs input from the third operational amplifier OP3 when the second switches SW2 are in the ON state is held by the capacitor C2 even after the second switches SW2 are bought into the OFF state, and the held voltage change amount ΔVs is output from the voltage change amount output terminal 45. Namely, during a period during which the operation of detecting the voltage change amount ΔVs is being performed, the second switches SW2 remain in the ON state, and the voltage change amount ΔVs input from the third operational amplifier OP3 is output as is through the fifth operational amplifier OP5. After the second switches SW2 are brought into the OFF state upon competition of the operation of detecting the voltage change amount ΔVs, the voltage change amount ΔVs held by the fifth operational amplifier OP5 is output.

The microprocessor 30 receives the voltage change amount ΔVs output from the voltage change amount output terminal 45 via the A/D input port 32, and converts it to a digital value. The voltage change amount ΔVs corresponds to a voltage drop produced by the element resistance Rpvs of the electromotive force cell 24 as a result of the flow of the constant current −Iconst therethrough. Therefore, the microprocessor 30 can detect (calculate) the element resistance Rpvs of the electromotive force cell 24 from the voltage change amount ΔVs.

Notably, the period of the operation of detecting the voltage change amount ΔVs; i.e., the period during which the second switches SW2 remain in the ON state, is controlled by the control section 59 (in the present embodiment, the period is set to 60 μsec). However, even after the second switches SW2 are switched to the OFF state, the voltage change amount ΔVs is held by the fifth operational amplifier OP5. Therefore, the microprocessor 30 is not required to acquire the voltage change amount ΔVs during the period of the operation of detecting the voltage change amount ΔVs (the 60 μsec period), and can acquire the held voltage change amount ΔVs at an arbitrary timing after the second switches SW2 are switched to the OFF state.

Upon completion of the operation of detecting the voltage change amount ΔVs, the control section 59 brings the second switches SW2 into the OFF state, and then switches the third switches SW3 from the OFF state to the ON state. The first switch SW1 remains in the OFF state. As a result of the third switches SW3 being brought into the ON state, a current path is formed starting from the current source 64 and extending through one of the third switches SW3, the connection path 41, the terminal Vs+ (the electrode 28), the electromotive force cell 24, the terminal COM (the electrode 22), the connection path 43, the other of the third switches SW3, and the current source 66 in this order. In this manner, the constant current +Iconst flows through the electromotive force cell 24.

This constant current +Iconst is opposite in polarity to the constant current −Iconst supplied to the electromotive force cell 24 during the period of the operation of detecting the voltage change amount ΔVs. The period during which the third switches SW3 remain in the ON state is set to 60 μsec as in the case of the period during which the second switches SW2 remain in the ON state. Notably, by supplying the constant current +Iconst having the opposite polarity to the electromotive force cell 24 as described above, it becomes possible to shorten a time needed to return to a normal state from a state in which the electromotive force cell 24 does not output a value of internal electromotive force reflecting the true oxygen concentration difference. This is because the internal electromotive force is affected by the orientation of the solid electrolyte member which constitutes the electromotive force cell 24.

The control section 59 brings the third switches SW3 into the OFF state after having supplied the constant current +Iconst to the electromotive force cell 24 for 60 μsec by bringing the third switches SW3 into the ON state. Subsequently, after elapse of a predetermined stabilization waiting time required for the electromotive force cell 24 to return to the normal state in which the electromotive force cell 24 outputs the value of internal electromotive force reflecting the true oxygen concentration difference, the first switch SW1 is returned to the ON state.

By virtue of the above-described control, the sensor element section control circuit 40 is temporarily switched from the state for performing the operation of detecting the gas detection signal Vip corresponding to the oxygen concentration, so as to perform the operation of detecting the voltage change amount ΔVs, which changes with the element resistance Rpvs of the electromotive force cell 24, and then returns to the state for performing the operation of detecting the gas detection signal Vip. During the period during which the operation of detecting the voltage change amount ΔVs is being performed, the gas detection signal Vip held at the time immediately before this period is output. Also, after completion of the operation of detecting the voltage change amount ΔVs, the voltage change amount ΔVs is held. This series of operations is controlled by the control section 59 in accordance with an instruction command SC (instruction signal) which is sent from the microprocessor 30 to the control section 59 through the serial transmission port 33 and which instructs the detection of the voltage change amount ΔVs.

Incidentally, in order to properly detect the gas detection signal Vip corresponding to the oxygen concentration, the pump cell 14 and the electromotive force cell 24 of the sensor element section 3 must be maintained at an appropriate activation temperature. Therefore, the microprocessor 30 periodically detects the voltage change amount ΔVs, and detects (calculates) the element resistance Rpvs of the electromotive force cell 24 from the voltage change amount ΔVs. The element resistance Rpvs has a correlation with the element temperature of the sensor element section 3. In view of this fact, a target resistance RT at which the element temperature becomes equal to the predetermined activation temperature is determined, and the supply of electric current to the heater section 4 is feedback-controlled by the heater section control circuit 70 such that the element resistance Rpvs becomes equal to the target resistance RT, whereby the sensor element section 3 is heated.

As described above, the control of the supply of electric current to the heater section 4 performed by the heater section control circuit 70 is PWM control. Therefore, switching noise may be generated at timings at which the state of energization of the heater section 4 is switched from the OFF state to the ON state and switched from the ON state to the OFF state. Accordingly, if the timing of switching the heater energization state overlaps with the timing of the operation of detecting the voltage change amount ΔVs by the sensor element section control circuit 40, due to influence of the switching noise, the voltage change amount ΔVs cannot be detected correctly.

In order to solve such a drawback, in the present embodiment, the timing of switching the heater energization state is prevented from overlapping with the period of the operation of detecting the voltage change amount ΔVs by the sensor element section control circuit 40.

Figure 2:
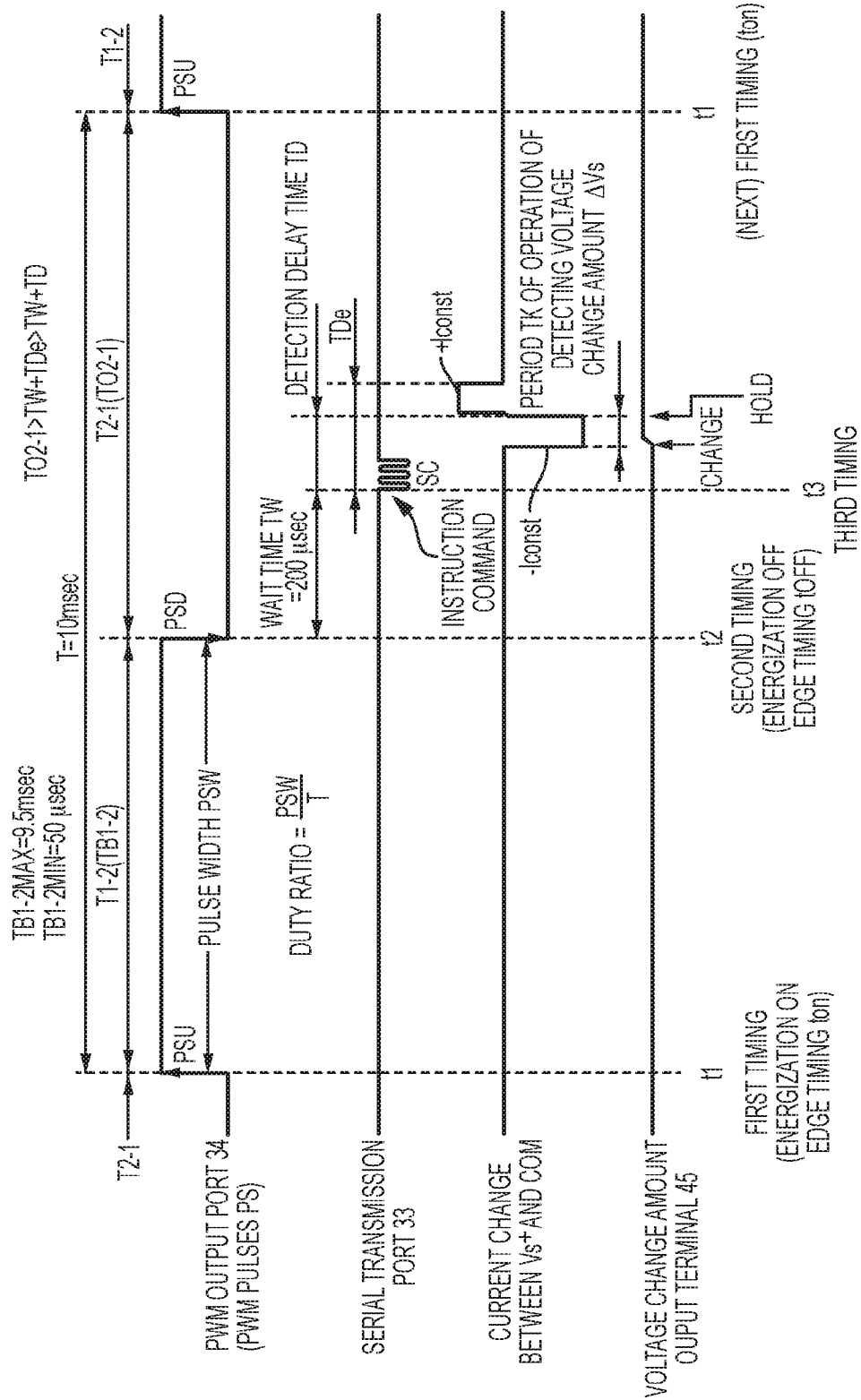
FIG. 2 is a timing chart showing operation timings of various sections of the gas sensor control apparatus according to the embodiment.

FIG. 2 is a timing chart showing the operation timings of the various portions of the gas sensor control apparatus 1 of the present embodiment.

In the present embodiment, the PWM pulses PS are output from the PWM output port 34 of the microprocessor 30, and the period T of the PWM pulses PS is set to 10 msec (fixed value). In the present embodiment, electric current is supplied to the heater section 4 (the energization state is the ON state) when the signal containing the PWM pulses PS is at the H level, and no electric current is supplied to the heater section 4 (the energization state is the OFF state) when the signal containing the PWM pulses PS is at the L level. Herein, the length of each period during which the signal containing the PWM pulses PS is at the H level will be referred as a pulse width PSW. Also, the ratio of the pulse width PSW to the period T will be referred to the duty ratio (ON duty ratio) of the PWM pulses PS. Notably, the PWM output port 34 functions in conjunction with a timer counter (not shown) incorporated in the microprocessor 30. Specifically, this timer counter includes a register for comparison with a count value corresponding to the period T of the PWM pulses PS, and a register for comparison with a count value corresponding to the pulse width PSW (duty ratio). The timer counter counters clock signals input to the microprocessor 30. Every time the count value of the timer counter becomes equal to the count value corresponding to the period T, the count value is reset, and the output of the PWM output port 34 changes from the L level to the H level. Also, every time the count value of the timer counter becomes equal to the count value corresponding to the pulse width PSW, the output of the PWM output port 34 changes from the H level to the L level.

Count values corresponding to the period T and the pulse width PSW (duty ratio) are set to the registers of the above-mentioned timer counter, and an output corresponding to the PWM output port 34 is turned on, whereby the PWM output port 34 starts its operation. During a period during which the period T and the pulse width PSW are not changed, the PWM pulses PS having a fixed period T and a fixed pulse width PSW are output successively. In the present embodiment, the period T is not changed from 10 msec; however, the pulse width PSW (duty ratio) is changed as a result of feedback control of the element resistance Rpvs performed such that it becomes equal to the target resistance RT. At this time, a first timing t1 (energization ON edge timing ton), at which the state of energization of the heater section 4 is switched from the OFF state to the ON state, corresponds to the leading edge PSU of each PWM pulse PS, and comes at fixed intervals corresponding to the period T. Notably, even when the set pulse width PSW (duty ratio) is changed, the output of the PWM output port 34 changes in synchronism with the leading edge PSU of each PWM pulse PS. Therefore, the interval between adjacent first timings t1 is always constant, and is equal to the period T (=10 msec). Meanwhile, a second timing t2 (energization OFF edge timing toff) at which the state of energization of the heater section 4 is switched from the ON state to the OFF state corresponds to the trailing edge PSD of each PWM pulse PS, and changes in accordance with the pulse width PSW.

In view of the foregoing, in the present embodiment, at a third timing t3 which comes after elapse of a predetermined wait time TW (=200 μsec) from the second timing t2, the microprocessor 30 sends an instruction command SC (instruction signal) instructing the detection of the voltage change amount ΔVs to the control section 59 of the sensor element section control circuit 40 through the serial transmission port 33. Upon receipt of the instruction command SC, the control section 59 of the sensor element section control circuit 40 performs the operation of detecting the voltage change amount ΔVs by the sensor element section control circuit 40.

The sensor element section control circuit 40 detects the voltage change amount ΔVs as described above. Specifically, the control section 59 brings the second switches SW2 of the sensor element section control circuit 40 in the ON state for a period of 60 μsec such that the constant current −Iconst is supplied to the electromotive force cell 24. The sensor element section control circuit 40 outputs the voltage change amount ΔVs corresponding to the difference between the potential at the terminal Vs+ (the electrode 28 of the electromotive force cell 24) at that time and the potential at the terminal Vs+ at a time immediately before that time. Then, the control section 59 brings the second switches SW2 into the OFF state so as to hold the voltage change amount ΔVs. Therefore, at least the 60 μsec period during which the second switches SW2 remain in the ON state (hereinafter referred to as the period TK of the operation of detecting the voltage change amount ΔVs: see FIG. 2) should not overlap with the timing of switching the heater energization state.

In view of this, in the present embodiment, the instruction command SC is output at the third timing t3, which comes after elapse of the wait time TW (=200 μsec) from the second timing t2 (energization OFF edge timing toff). Therefore, even when the second timing t2 changes, the second timing t2 does not overlap with the 60 μsec period TK of the operation of detecting the voltage change amount ΔVs.

Notably, in the present embodiment, the output of the instruction command SC at the third timing t3 is performed every 10-th period T of the PWM pulses PS. Accordingly, the detection of the voltage change amount ΔVs is performed at intervals of 100 msec, which is ten times the period T (=10 msec) of the PWM pulses PS.

Incidentally, the pulse width PSW (duty ratio) of the PWM pulses PS is determined as a result of feedback control (PID control) of the supply of electric current to the heater section 4 such that the element resistance Rpvs becomes equal to the target resistance RT. Therefore, in a period during which the element temperature of the sensor element section 3 is low, a control for increasing the pulse width PSW (duty ratio) is performed. Thus, if the interval between the second timing t2 and the first timing t1 which comes after the second timing t2 decreases, the period TK of the operation of detecting the voltage change amount ΔVs may overlap with the switching of the energization state of the heater section 4 at the first timing t1 which comes next.

In order to avoid such a possibility, in the present embodiment, the period TK of the operation of detecting the voltage change amount ΔVs is determined such that it overlaps with neither the second timing t2 nor the first timing t1 which comes next.

Notably, in the following description, the period between a first timing t1 and a second timing t2 which comes after that will be referred to as a 1-2 period $T_{1-2}$, and the period between a second timing t2 and a first timing t1 which comes after that will be referred to as a 2-1 period $T_{2-1}$. Also, as described above, in the present embodiment, every time the period which is equal to 10 times the period T of the PWM pulses PS elapses, the instruction command SC is output so as to detect the voltage change amount ΔVs. In view of this, of the 2-1 periods $T_{2-1}$, 2-1 periods $T_{2-1}$ including the third timing t3 at which the instruction command SC is output will be referred to as output 2-1 period $TO_{2-1}$, and, of the 1-2 periods $T_{1-2}$, 1-2 periods $T_{1-2}$ immediately before the output 2-1 period $TO_{2-1}$ will be referred to as pre-output 1-2 period $TB_{1-2}$ (see FIG. 2).

In order to prevent the period TK of the operation of detecting the voltage change amount ΔVs from overlapping with the first timing t1 which comes next, the output 2-1 period $TO_{2-1}$ must be rendered longer than the sum of the wait time TW (=200 μsec) between the second timing t2 and the third timing t3 (output of the instruction command SC) and a detection delay time TD between the commencement of the output of the instruction command SC and the completion of the operation of detecting the voltage change amount ΔVs (in the present embodiment, the detection delay time TD is about 180 μsec including the detection operation period TK of 60 μsec). In view of this, in the present embodiment, the maximum value $TB_{1-2max}$ of the pre-output 1-2 period $TB_{1-2}$ is determined such that the output 2-1 period $TO_{2-1}$ become longer the sum of the wait time TW and the detection delay time TD. Thus, even when an operation for increasing the pulse width PSW (duty ratio) of the PWM pulses PS is performed, the length of the pre-output 1-2 period $TB_{1-2}$ is restricted to the maximum value $TB_{1-2max}$ or less when the operation of detecting the voltage change amount ΔVs is performed (in the periods T in which the instruction command SC is output). However, in the present embodiment, a period of about 250 μsec (the detection delay time TD (about 180 μsec)+the time required to complete the supply of the constant current +Iconst) is referred to as a detection delay time TDe, and the maximum value $TB_{1-2max}$ of the pre-output 1-2 period $TB_{1-2}$ is determined such that the output 2-1 periods $TO_{2-1}$ become longer the sum of the wait time TW and the detection delay time TDe.

However, if control is performed such that the restriction by the maximum value $TB_{1-2max}$ is applied to the pre-output 1-2 period $TB_{1-2}$ of the 1-2 periods $T_{1-2}$ and is not applied to the remaining 1-2 periods $T_{1-2}$, the control becomes complex. In view of this, in the present embodiment, the maximum value $TB_{1-2max}$ is set to 9.5 msec, and the length of all the 1-2 periods $T_{1-2}$ including the pre-output 1-2 period $TB_{1-2}$ is restricted to the maximum value $TB_{1-2max}$ (9.5 msec) or less. Namely, the maximum value of the pulse width PSW is set to 9.5 msec, and the maximum value of the duty ratio is set to 95% (=9.5/10.0×100).

By virtue of such setting, all the 2-1 periods $T_{2-1}$, including the output 2-1 period $TO_{2-1}$, can have a length of 500 μsec. This length of 500 μsec is longer the sum of the wait time TW (=200 μsec) from the second timing t2 to the third timing t3 and the detection delay time TD (about 180 μsec) between the output of the instruction command SC and the completion of the operation of detecting the voltage change amount ΔVs. Therefore, in the present embodiment, the period TK of the operation of detecting the voltage change amount ΔVs does not overlap with the first timing t1 which comes next. Notably, in the present embodiment, this length of 500 μsec is rendered longer than the sum of the wait time TW and the detection delay time TDe (about 250 μsec).

Also, in the present embodiment, the minimum value $TB_{1-2min}$ of the length of the pre-output 1-2 period $TB_{1-2}$ is set to 50 μsec in advance. Also, the length of all the 1-2 periods $T_{1-2}$, including the pre-output 1-2 period $TB_{1-2}$, is restricted to the minimum value $TB_{1-2min}$ (50 μsec) or greater. Namely, the minimum value of the pulse width PSW is set to 50 μsec, and the minimum value of the duty ratio is set to 0.5%. By virtue of this setting, even when a control for decreasing the pulse width PSW (duty ratio) of the PWM pulses PS is performed, it is possible to prevent occurrence of a state in which the duty ratio becomes 0% and the output of the PWM pulses PS stops. Namely, the first timing t1 and the second timing t2 are present without fail. Therefore, the third timing t3 subsequent to the second timing t2 can be secured, and the voltage change amount ΔVs can be detected without fail.

Figure 3:
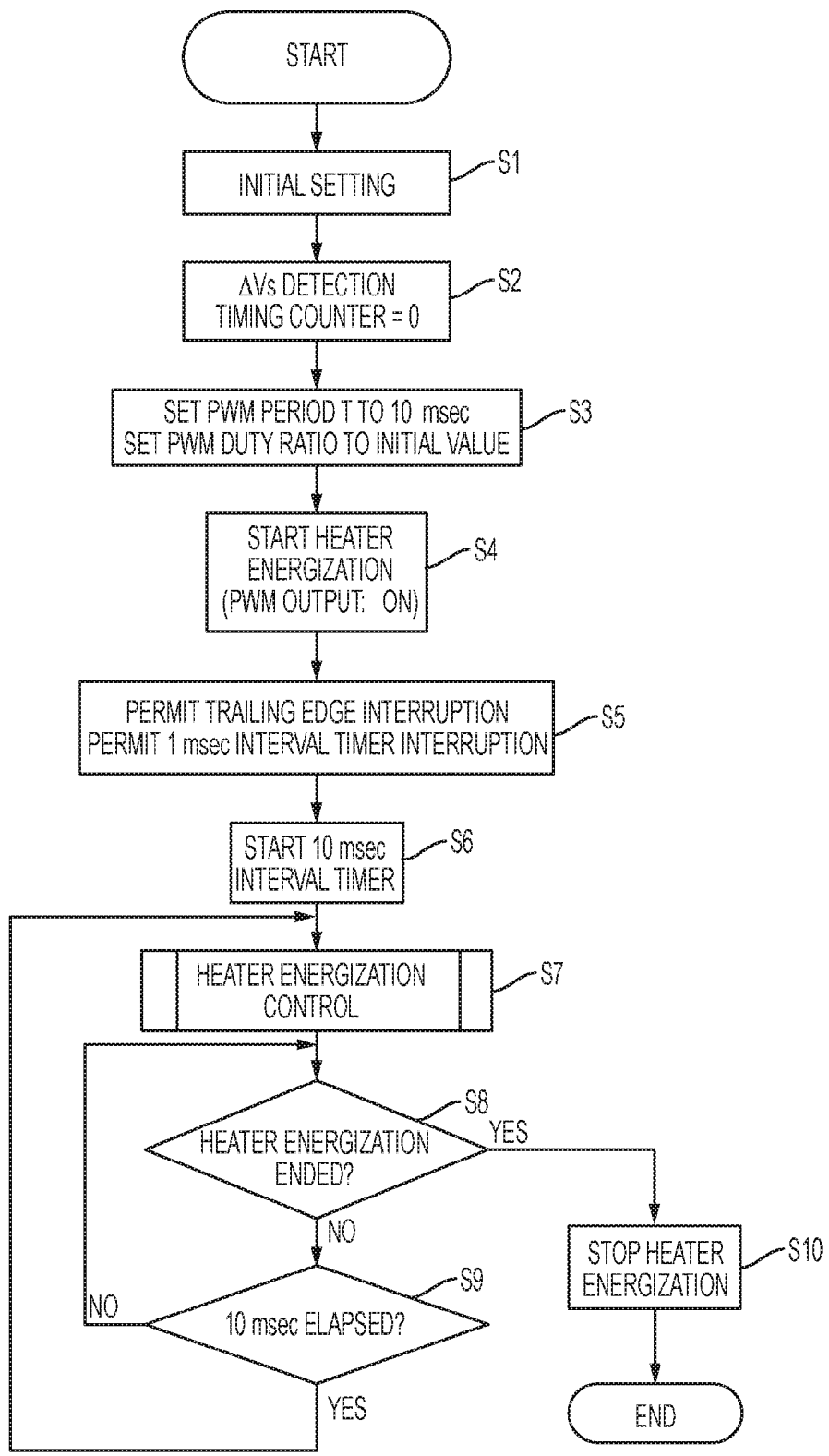
FIG. 3 is a flowchart showing processing operation of a microprocessor of the gas sensor control apparatus according to the embodiment.

Next, the operation of the gas sensor control apparatus 1 (in particular, the microprocessor 30) according to the present embodiment will be described with reference to the flowchart of FIG. 3.

First, when an ignition key (not shown) is turned on, the microprocessor 30 of the gas sensor control apparatus 1 starts upon supply of electric power thereto. In step S1, the microprocessor 30 performs a necessary initial setting.

In step S2 subsequent thereto, the microprocessor 30 resets the ΔVs detection timing counter to zero. Next, the microprocessor 30 proceeds to step S3 in order to perform the initial setting of the PWM output port 34 of the microprocessor 30 and the timer counter which functions in conjunction with the PWM output port 34, to thereby set the PWM period T to 10 msec and set the PWM duty ratio to an initial value. Notably, this initial value is determined on the basis of the control performed during a pre-heating period before the sensor element section 3 becomes active. However, in the flowing description, the control during the pre-heating period will not be described. Next, the microprocessor 30 proceeds to step S4 so as to bring the PWM output port 34 of the microprocessor 30 into the ON state, to thereby start the energization of the heater section 4.

Next, the microprocessor 30 proceeds to step S5 so as to permit trailing edge interruptions (interruptions generated at the trailing edges of the PWM pulses PS). The trailing edge interruptions are generated by the timer counter which functions in conjunction with the PWM output port 34. Also, the microprocessor 30 permits interruptions generated by a 1 msec interval timer which operates separately from the timer counter. Further, in step S6, the microprocessor 30 starts a 10 msec interval timer used for measuring the intervals of the energization control for the heater section 4. Notably, the intervals of 10 msec measured by this timer are rendered equal to the PWM period T (=10 msec).

After that, the microprocessor 30 proceeds to step S7, and executes a heater energization control routine, described below, so as to calculate the PWM duty ratio and output the PWM pulses PS, whereby the energization of the heater section 4 is controlled. Also, in step S8 subsequent thereto, the microprocessor 30 determines whether or not an end instruction which instructs the microprocessor 30 to end the heater energization control has been issued because, for example, the engine has been stopped. In the case where the end instruction has not yet been issued (No), the microprocessor 30 proceeds to step S9.

Meanwhile, when the instruction for ending the heater energization control is issued because, for example, the engine has been stopped, the microprocessor 30 makes a "Yes" determination in step S8, and then proceeds to step S10. In step S10, the microprocessor 30 stops the timers and interruptions started or permitted in steps S5 and S6, and brings the output of the PWM output port 34 of the microprocessor 30 into the OFF state so as to stop the supply of electric current to the heater section 4. After that, the microprocessor 30 ends the present control program.

In step S9, the microprocessor 30 determines, through use of the 10 msec interval timer started in step S6, whether or not 10 msec, which is the interval of the energization control for the heater section 4, has elapsed. In the case where 10 msec has not yet elapsed (No), the microprocessor 30 returns to step S8, and repeats step S8 and step S9. Thus, while monitoring the instruction for ending the heater energization control in step S8, the microprocessor 30 waits for an elapse of 10 msec in step S9. When 10 msec has elapsed, the microprocessor 30 makes a "Yes" determination in step S9, and returns to step S7 so as to repeat the energization control for the heater section 4 at intervals of 10 msec. Notably, while repeating the above-described steps S7 to S9, the microprocessor 30 executes a timer interruption routine, described below, at intervals of 1 msec. Also, the microprocessor 30 executes a trailing edge interruption routine, which will be described later, at the trailing edge PSD of each PWM pulse PS.

Next, a 1 msec-interval-timer interruption routine will be described with reference to the flowchart of FIG. 4. In the period during which the steps S7 to S9 of FIG. 3 are executed, timer interruption occurs at intervals of 1 msec, and the present routine is executed.

First, in step S21, the microprocessor 30 samples, through the A/D input port 31, the gas detection signal Vip output from the gas detection signal output terminal 44 of the sensor element section control circuit 40.

Next, in step S22, the microprocessor 30 performs processing of averaging the sampled values of the gas detection signal Vip every time the sampling is performed a predetermined number of times. In step S23 subsequent thereto, the microprocessor 30 calculates a gas concentration on the basis of the averaged value of the gas detection signal Vip. In step S24 subsequent thereto, the microprocessor 30 stores the calculated gas concentration in a predetermined memory.

Next, in step S25, the microprocessor 30 samples, through the A/D input port 32, the voltage change amount ΔVs output from the voltage change amount output terminal 45 of the sensor element section control circuit 40.

Subsequently, in step S26, the microprocessor 30 performs processing of averaging the sampled voltage change amounts ΔVs every time the sampling is performed a predetermined number of times. In step S27 subsequent thereto, the microprocessor 30 calculates the element resistance Rpvs on the basis of the voltage change amount ΔVs. In step S28 subsequent thereto, the microprocessor 30 stores the calculated element resistance Rpvs in a predetermined memory. After that, the microprocessor 30 ends this 1 msec-interval-timer interruption routine.

Next, a trailing edge interruption routine will be described with reference to the flowchart of FIG. 5. In the period during which the steps S7 to S9 of FIG. 3 are executed, the timer counter, which functions in conjunction with the PWM output port 34, generates an interruption every time the trailing edge PSD of each PWM pulse PS (the second timing t2) comes, whereby the present routine is executed.

First, in step S31, the microprocessor 30 prohibits the above-mentioned timer interruption at intervals of 1 msec. Thus, during a period during which the trailing edge interruption routine is being executed, the timer interruption at intervals of 1 msec is not accepted, and the present edge interruption processing is performed preferentially. In step S32 subsequent thereto, the microprocessor 30 increases the value of the ΔVs detection timing counter by 1 (increment). Next, in step S33, the microprocessor 30 determines whether or not the value of the ΔVs detection timing counter is 10. In the case where the value of the ΔVs detection timing counter is not 10 (No), the microprocessor 30 proceeds to step S38. Meanwhile, when the value of the ΔVs detection timing counter reaches 10, the microprocessor 30 makes a "Yes" determination in step S33, and proceeds to step S34. In step S34, the microprocessor 30 resets the value of the ΔVs detection timing counter to 0. Accordingly, steps S34 to S37 are executed only one time every time the trailing edge PSD of each PWM pulse PS (the second timing t2) occurs 10 times.

In step S35 subsequent to step S34, the microprocessor 30 starts a timer for clocking the time of 200 μsec (wait time TW).

In step S36 subsequent thereto, the microprocessor 30 waits until the 200 μsec timer started in step S35 is up. That is, until the timer is up (No), the microprocessor 30 repeats step S36. When 200 μsec (wait time TW) has elapsed and the timer is up (Yes: third timing t3), the microprocessor 30 proceeds to step S37.

In step S37, the microprocessor 30 sends, through the serial transmission port 33, the instruction command SC (instruction signal) for instructing the detection of the voltage change amount ΔVs to the control section 59 of the sensor element section control circuit 40. Upon completing the transmission of the instruction command SC, the microprocessor 30 proceeds to step S38. Upon receiving the instruction command SC, the control section 59 of the sensor element section control circuit 40 performs the above-described operation of detecting the voltage change amount ΔVs. Notably, the above-mentioned detection delay time TD of about 180 μsec as measured from the start of transmission of the instruction command SC is required for the microprocessor 30 to obtain and hold the voltage change amount ΔVs detected in the detection operation period TK and output from the voltage change amount out terminal 45 of the sensor element section control circuit 40. Notably, the detection delay time TDe including the time required to compete the supply of the constant current +Iconst is about 250 μsec (see FIG. 2).

In step S38, the microprocessor 30 again permits the timer interruption at intervals of 1 msec once prohibited, and ends this interruption routine.

Figure 6:
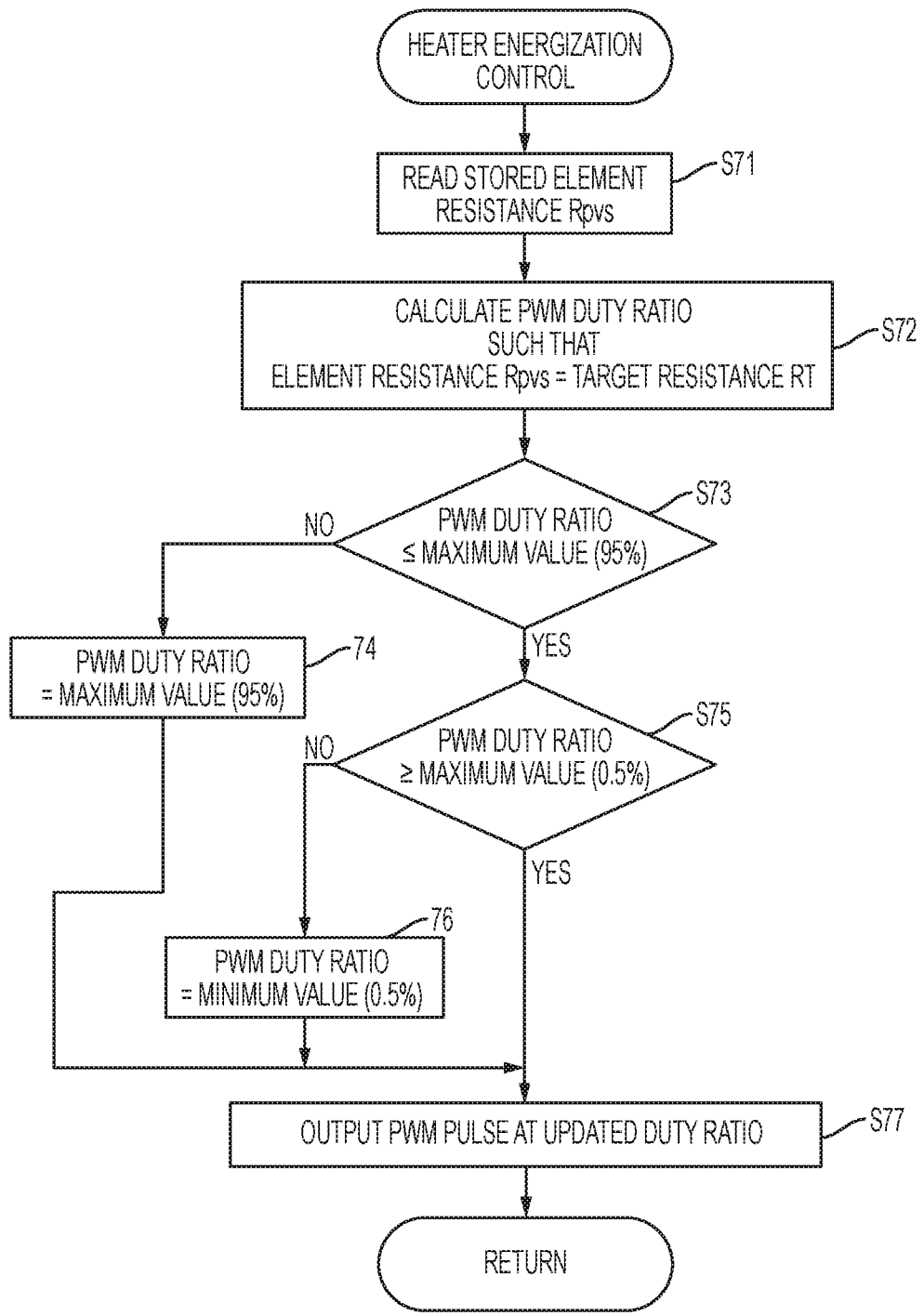
FIG. 6 is a flowchart showing the details of a heater energization control routine.

Next, a heater energization control routine will be described with reference to the flowchart of FIG. 6. As described above, the present routine is executed in step S7 of FIG. 3 at intervals of 10 msec.

Figure 4:
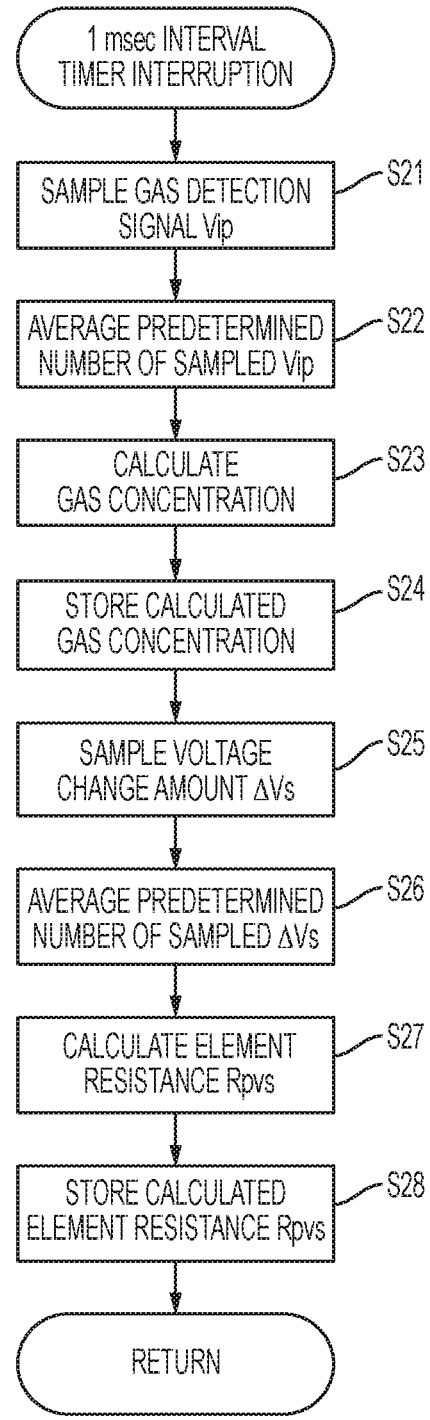
FIG. 4 is a flowchart showing the details of a timer interruption routine.

First, in step S71, the microprocessor 30 reads out from the memory the element resistance Rpvs stored in step S28 of FIG. 4. Next, in step S72, the microprocessor 30 calculates the PWM duty ratio by means of PID control such that the read element resistance Rpvs coincides with the target resistance RT.

Next, the microprocessor 30 proceeds to step S73, and determines whether or not the calculated PWM duty ratio is equal to or less than the maximum value (95%) (i.e., whether or not the pulse width PSW is equal to or less than the maximum value $TB_{1-2max}$ (=9.5 msec). In the case where the calculated PWM duty ratio is equal to or less than the maximum value (95%) (Yes), the microprocessor 30 proceeds to step S75. Meanwhile, in the case where the calculated PWM duty ratio is greater than the maximum value (95%) (No), the microprocessor 30 proceeds to step S74 so as to set the PWM duty ratio to the maximum value (95%), and then proceeds step S77. As a result, a period of 500 μsec is secured between the trailing edge PSD (the second timing t2) of each PWM pulse PS and the leading edge PSU (the first timing t1) of another PWM pulse PS which comes next. As described above, the length of this 500 μsec period is greater than the sum of the wait time TW (=200 μsec) and the detection delay time TD (about 180 μsec). Furthermore, in the present embodiment, the length of this 500 μsec period is rendered greater than the sum of the wait time TW (=200 μsec) and the detection time TDe (about 250 μsec).

In step S75, the microprocessor 30 determines whether or not the calculated PWM duty ratio is equal to or greater than the minimum value (0.5%) (i.e., whether or not the pulse width PSW is equal to or greater than the minimum value $TB_{1-2min}$ (=50 μsec)). In the case where the calculated PWM duty ratio is equal to or greater than the minimum value (0.5%) (Yes), the microprocessor 30 proceeds to step S77. Meanwhile, in the case where the calculated PWM duty ratio is less than the minimum value (0.5%) (No), the microprocessor 30 proceeds to step S76 so as to set the PWM duty ratio to the minimum value (0.5%), and then proceeds to step S77. As a result, a period of 50 μsec is secured between the leading edge PSU (the first timing t1) of each PWM pulse PS and the trailing edge PSD (the second timing t2) thereof which comes next, whereby the first timing t1 and the second timing t2 are present without fail.

In step S77, the microprocessor 30 outputs a PWM pulse PS from the PWM output port 34 at the updated PWM duty ratio, and then ends this heater energization control routine. Notably, the output of the PWM pulse PS from the PWM output port 34 at the updated PWM duty ratio changes in synchronism with the leading edge PSU (the first timing t1) of the next PWM pulse PS. The next second timing t2 (the trailing edge PSD) changes in accordance with the updated pulse width PSW of the PWM pulse PS, and the trailing edge interruption is generated at the new second timing t2.

Thus, the PWM duty ratio is controlled such that the period TK of the operation of detecting the voltage change amount ΔVs overlaps with neither the second timing t2 (the trailing edge PSD) nor the first timing t1 (the leading edge PSU) which comes next. By virtue of such control, switching noise generated as a result of switching of the heater energization state is prevented from affecting the detection of the voltage change amount ΔVs (accordingly, the detection of the element resistance Rpvs). Therefore, the element resistance Rpvs can be detected without fail.

Notably, in the present embodiment, the voltage change amount ΔVs corresponds to the response change amount in the present invention, and the sensor element section control circuit 40 which performs the operation of detecting the voltage change amount ΔVs corresponds to the change amount detection means in the present invention.

The microprocessor 30 which executes steps S25 to S28 corresponds to the element resistance detection means for detecting the element resistance Rpvs.

The microprocessor 30 which executes steps S32 to S37 corresponds to the instruction signal output means, and the instruction command SC transmitted (output) in step S37 corresponds to the instruction signal.

The heater section control circuit 70, the PWM output port 34 of the microprocessor 30, and the microprocessor 30 which executes step S4 and steps S71 to S77 correspond to the heater energization control means.

Of the heater energization control means, the microprocessor 30 which executes steps S73 to S74 corresponds to the maximum value control means. The microprocessor 30 which executes steps S75 to S76 corresponds to the minimum value control means.

As described above, the gas sensor control apparatus 1 of the present embodiment includes the instruction signal output means (see FIG. 5: steps S32 to S37) which outputs the instruction command SC (instruction signal) for instructing the detection of the voltage change amount ΔVs to the sensor element section control circuit 40 (change amount detection means) at the third timing t3 after elapse of the wait time TW (=200 μsec) from the second timing t2 (energization OFF edge timing toff).

By virtue of this configuration, the switching of the state of energization of the heater section 4 at the second timing t2 does not overlap with the period TK of the operation of detecting the voltage change amount ΔVs. Therefore, switching noise generated as a result of at least the switching of the heater energization state at the second timing t2, which changes with the pulse width PSW, is prevented from affecting the detection of the voltage change amount ΔVs (accordingly, the detection of the element resistance Rpvs). Accordingly, the element resistance Rpvs can be detected properly.

In addition, since the required operation is merely outputting the instruction command SC (instruction signal) at the third timing t3 after elapse of the wait time TW (=200 μsec) from the second timing t2 (energization OFF edge timing toff); i.e., the trailing edge PSD of each PWM pulse PS, complicated control for timing adjustment is not required, whereby the processing of the microprocessor 30 can be simplified.

Further, in the gas sensor control apparatus 1 of the present embodiment, the heater energization control means (see FIG. 6: steps S71 to S77) feedback-controls the supply of electric current to the heater section 4 such that the detected element resistance Rpvs becomes equal to the target resistance RT. As a result, the sensor element section 3 can be maintained at a proper activation temperature, whereby the gas concentration can be detected properly.

Further, in the gas sensor control apparatus 1 of the present embodiment, every time a period of time 10 times the PWM period T (=10 msec) elapses; in other words, every time the period T occurs 10 times (10 periods), the instruction command SC (instruction signal) is output so as to detect the voltage change amount ΔVs. By virtue of this configuration, the voltage change amount ΔVs and the element resistance Rpvs based thereon can be detected regularly. In addition, the interval of the detection (update) of the element resistance Rpvs can be made longer than the period T of the PWM pulses PS for controlling the supply of electric current to the heater section 4 (in the present embodiment, 100 msec interval 10 times the period T (=10 msec)). Therefore, when the energization of the heater section 4 is feedback-controlled, the control can be performed stably by suppressing oscillation or the like.

Moreover, in the gas sensor control apparatus 1 of the present embodiment, the length of all the 1-2 periods $T_{1-2}$, including the pre-output 1-2 period $TB_{1-2}$, is restricted to the maximum value $TB_{1-2max}$ (=9.5 msec) or less. This maximum value $TB_{1-2max}$ is determined to fall within a range in which the length of the output 2-1 period $TO_{2-1}$ becomes longer than the sum of the wait time TW and the detection delay time TDe. Therefore, the period TK of the operation of detecting the voltage change amount ΔVs does not overlap with the switching of the heater energization state at the first timing t1. By virtue of this configuration, switching noise generated as a result of the switching of the heater energization state at the first timing t1, which comes at constant intervals corresponding to the period T, is also reliably prevented from affecting the detection of the voltage change amount ΔVs (accordingly, the detection of the element resistance Rpvs). Accordingly, the element resistance Rpvs can be detected more properly.

In addition, in the present embodiment, since the same maximum value $TB_{1-2max}$ is used for the periods T in which the instruction command SC (instruction signal) is output, and for the remaining periods T, the control becomes simple.

Further, in the gas sensor control apparatus 1 of the present embodiment, the length of all the 1-2 periods $T_{1-2}$ is restricted to the minimum value $TB_{1-2min}$ (=50 μsec) or greater. By virtue of this configuration, the length of the 1-2 periods $T_{1-2}$ is restricted to the minimum value $TB_{1-2\ min}$ (greater than zero) or greater, and the first timing t1 and the second timing t2 are present without fail. Therefore, the third timing t3 subsequent to the second timing t2 can be also secured, whereby the timing for detecting the voltage change amount ΔVs (output of the instruction command SC at the third timing t3) is not missed. Thus, the element resistance Rpvs can be detected reliably and regularly.

In addition, in the present embodiment, since the same minimum value $TB_{1-2min}$ is used for the periods T in which the instruction signal SC is output and the remaining periods T, the control becomes simple.

Moreover, in the gas sensor control apparatus 1 of the present embodiment, the state of energization of the heater section 4 is switched from the OFF state to the ON state at the first timing t1, and switched from the ON state to the OFF state at the second timing t2. Namely, electric current is supplied to the heater section 4 during the 1-2 periods $T_{1-2}$. Accordingly, the minimum value $TB_{1-2min}$ of the length of the pre-output 1-2 period becomes the minimum value (greater than 0) of the length of the period during which electric current is supplied to the heater section 4. This minimum length is shorter than the minimum length (>the wait time TW+the detection delay period TDe) for the case where electric current is supplied to the heater section 4 during the 2-1 periods $T_{2-1}$, contrary to the above-described case. Therefore, in the case where the supply of electric current to the heater section 4 is unnecessary or is required for a very short period of time, the length of the period during which electric current is supplied to the heater section 4 can be shortened to the minimum length (the minimum value) $TB_{1-2min}$ (in the present embodiment, 50 μsec) of the pre-output 1-2 period. Accordingly, it is possible to properly control the energization of the heater section 4 while reducing the consumption of electric power by the heater section 4.

First Modification

Figure 7:
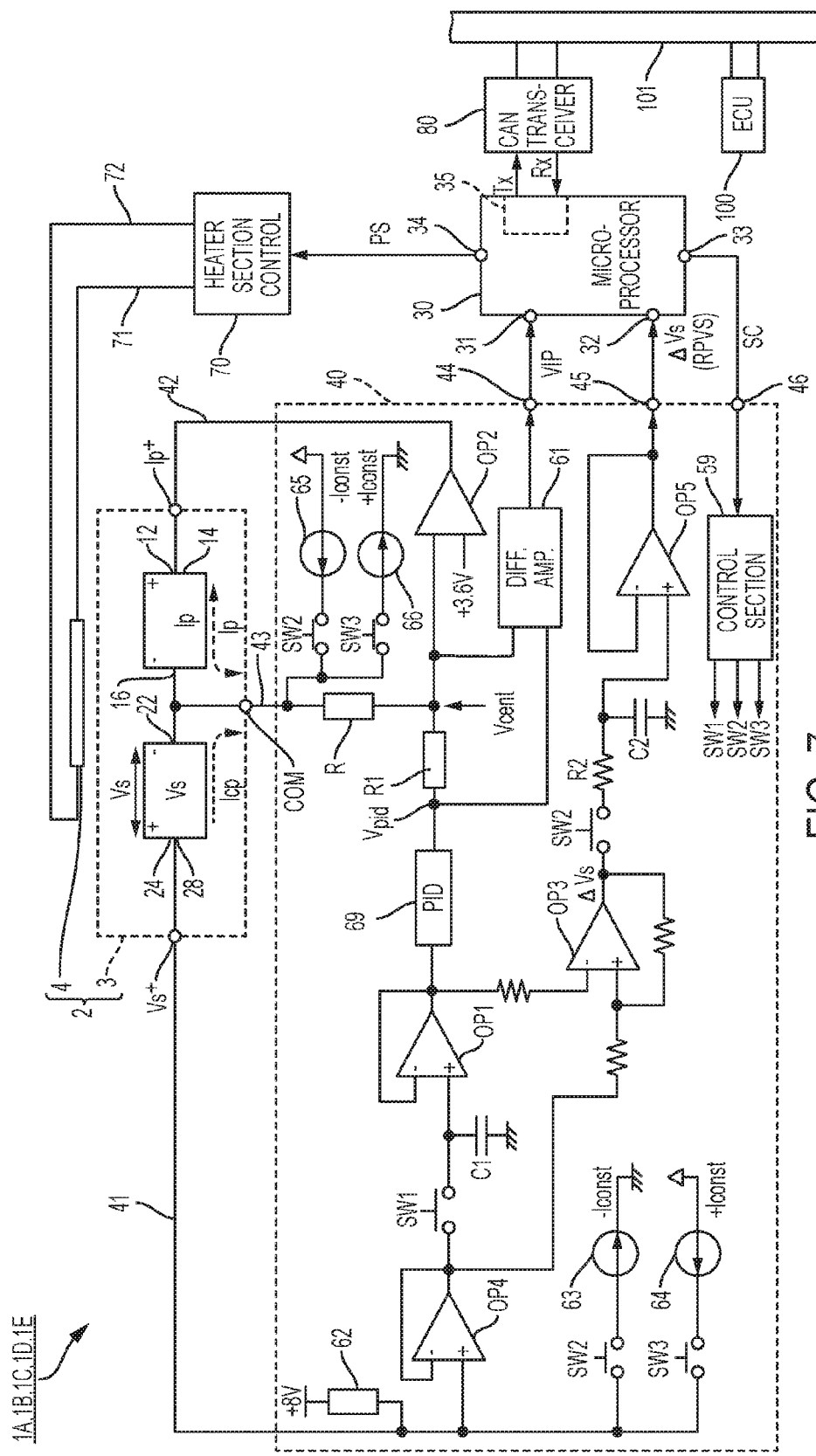
FIG. 7 is an explanatory diagram schematically showing the configuration of a gas sensor control apparatus according to first through fifth modifications.

Next, a first modification of the above-described embodiment will be described with reference to the drawings. FIG. 7 is a diagram schematically showing the configuration of a gas sensor control apparatus 1A according to the first modification. This gas sensor control apparatus 1A has a configuration similar to that of the gas sensor control apparatus 1 according to the above-described embodiment. In addition, the microprocessor 30 comprises means (hereinafter referred to as prevention means) for preventing use of the voltage change amount ΔVs (the response change amount) which have been affected by transmission of data (such as those representing the measured gas concentration) to an ECU 100, which is an external device, and use of the element resistance Rpvs obtained therefrom.

As shown in FIG. 7, the microprocessor 30 includes a CAN (controller area network) protocol controller 35, which is connected to a CAN bus 101 via a CAN transceiver 80 provided outside the microprocessor 30. The microprocessor 30 transmits data (CAN transmission data Tx), such as those representing the measured gas concentration, to the ECU 100 connected to the CAN bus 101. Also, the microprocessor 30 receives data (CAN reception data Rx) from the ECU 100. Notably, when the microprocessor 30 transmits data to the ECU 100, the consumed current increases, in particular, at the CAN transceiver 80 due to transmission of the data. This may result in a change in the power supply voltage of the microprocessor 30 and control circuits such as the sensor element section control circuit 40.

Figure 8:
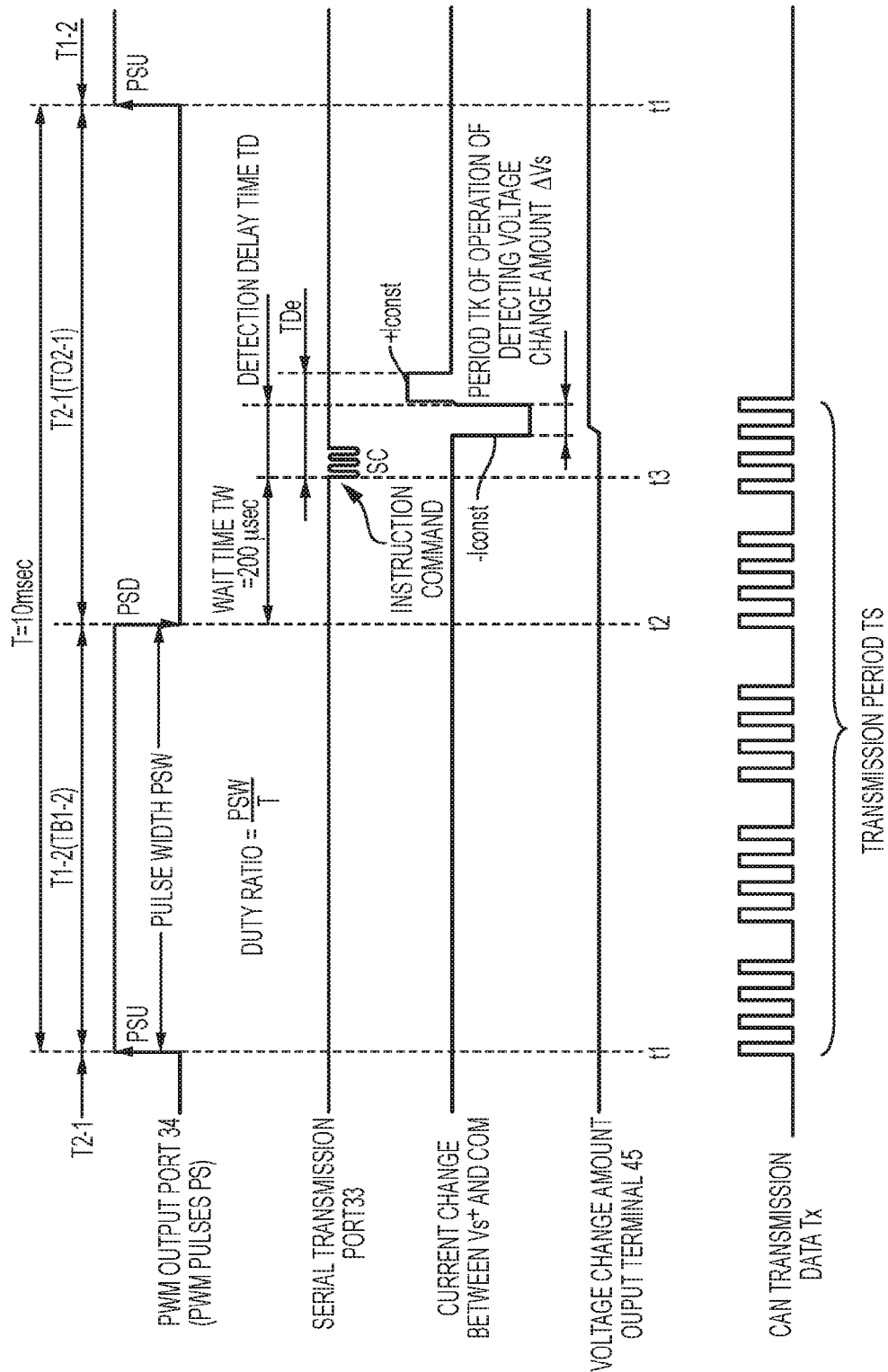
FIG. 8 is a timing chart showing operation timings of various sections of the gas sensor control apparatus according to the first through fifth modifications.

Therefore, as shown in FIG. 8, in the case where at least a portion of the period TK (detection period) of the operation of detecting the voltage change amount ΔVs (response change amount) subsequent to the output of the instruction command SC (instruction signal) at the third timing t3 overlaps with the transmission of the CAN transmission data Tx (transmission period TS), the voltage change amount ΔVs and the element resistance Rpvs detected on the basis of the voltage change amount ΔVs are affected, and proper detection of the element resistance Rpvs may become impossible. In order to overcome such a problem, the gas sensor control apparatus 1A of the first modification includes the above-described prevention means for eliminating such influence. Notably, the gas sensor control apparatus 1A of the first modification is identical with the gas sensor control apparatuses 1B, 1C, 1D, and 1E of second to fifth modifications described below in the point that the prevention means is provided. However, the first through fifth modifications differ from one another in the configuration of the prevention means. In the following description, a description of portions similar to those of the embodiment will be omitted or such portions will be described only briefly.

In the present first modification, specifically, prior to the output of the instruction command SC (instruction signal) at the third timing t3, a determination is made as to whether or not the transmission of data (CAN transmission data Tx) to the ECU 100 is being performed at a timing (pre-output determination timing) before the third timing t3 (pre-output transmission determination means). In the case where it is determined that the transmission of data is being performed, the output of the instruction command SC at the third timing t3 is stopped (output stopping means).

Moreover, in the present first modification, in the case where the output of the instruction command SC at the third timing t3 is stopped, the instruction command SC is output at the third timing t3 in a period T subsequent to the period T in which the output of the instruction command SC at the third timing t3 was stopped. Namely, the period T in which the instruction command SC is output is postponed (period postponing output means).

In the present first modification, the microprocessor 30 which executes the pre-output transmission determination means, the output stopping means, and the period postponing output means corresponds to the prevention means.

Figure 9A:
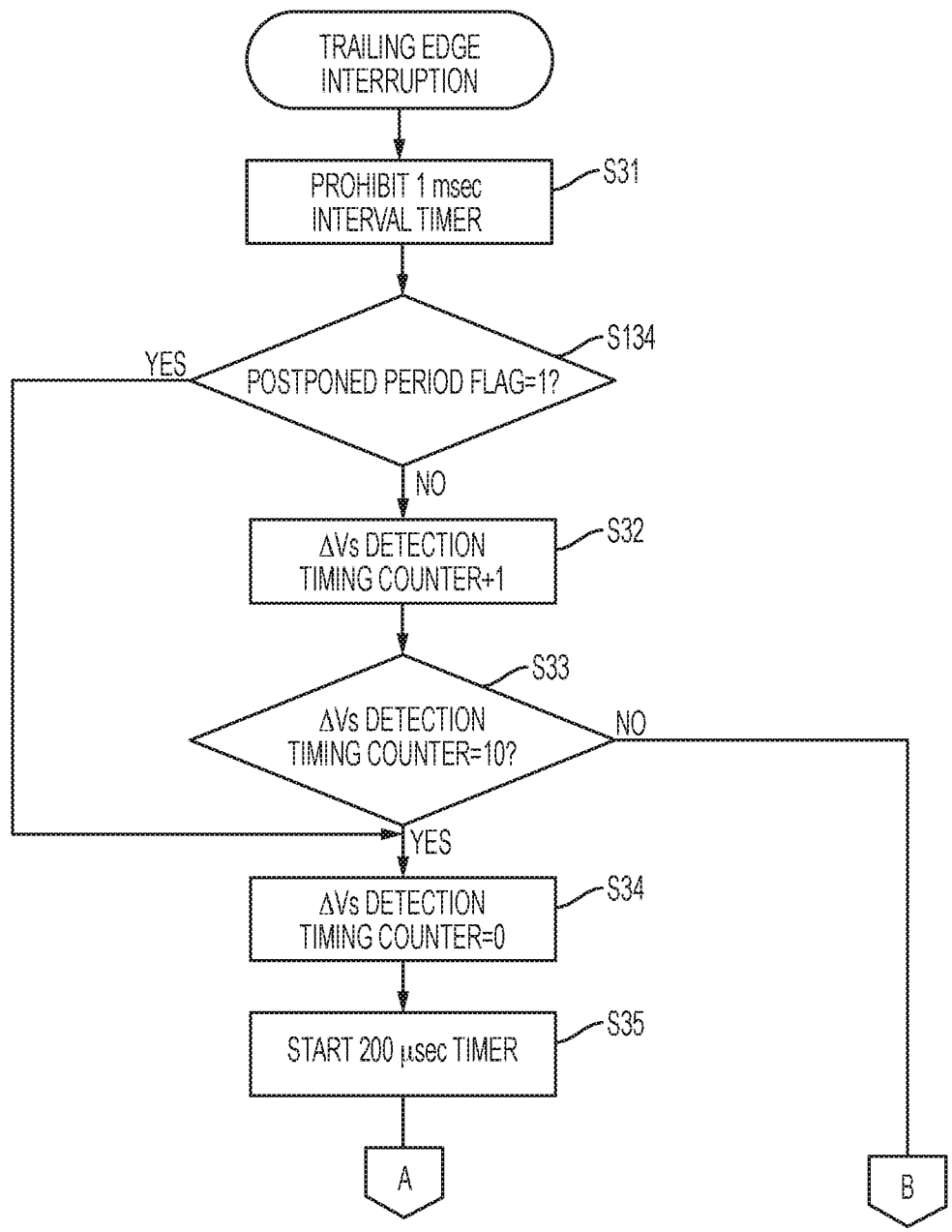
FIGS. 9A and 9B are flowcharts showing the details of a trailing edge interruption routine according to the first modification.
Figure 9B:
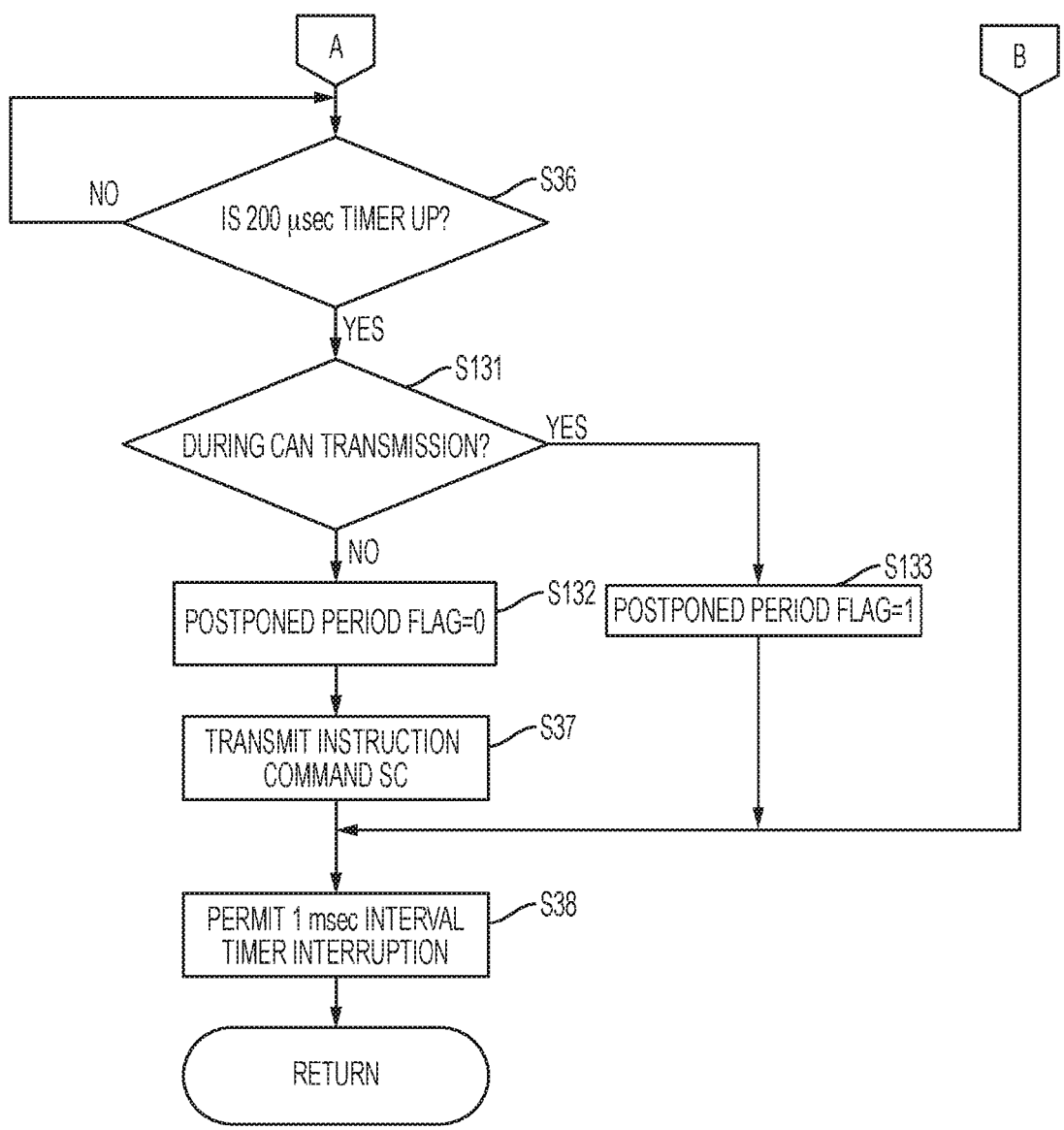

Next, of the processing operation of the microprocessor 30 of the gas sensor control apparatus 1A according to the present first modification, the trailing edge interruption routine will be described with reference to the flowcharts of FIGS. 9A and 9B. In FIGS. 9A and 9B, steps which are the same as those in the trailing edge interruption routine according to the embodiment shown in FIG. 5 are denoted by the same reference numerals (this rule also applies to the second through fifth modifications). Also, since the remaining processing operation of the microprocessor 30 is the same as that in the embodiment, only the trailing edge interruption routine will be described below, and the descriptions of the remaining routines will not be repeated.

First, in step S31, the microprocessor 30 prohibits the timer interruption at intervals of 1 msec (see FIG. 4). Next, in S134, the microprocessor 30 determines whether or not a postponed period flag, described below, is 1. In the case where the postponed period flag is 0 (No), the microprocessor 30 proceeds to step S32.

In step S32 subsequent thereto, the microprocessor 30 increases the value of the ΔVs detection timing counter by 1 (increment). Next, in step S33, the microprocessor 30 determines whether or not the value of the ΔVs detection timing counter is 10. In the case where the value of the ΔVs detection timing counter is not 10 (No), the microprocessor 30 proceeds to step S38. Meanwhile, when the value of the ΔVs detection timing counter reaches 10, the microprocessor 30 makes a "Yes" determination in step S33, and proceeds to step S34. Thus, in the case where the postponed period flag is 0 (ordinary case), step S34 and steps subsequent thereto are executed only one time every time the trailing edge PSD of each PWM pulse PS (the second timing t2) occurs 10 times, and the voltage change amount ΔVs is detected every time the PWM period T (10 msec) occurs 10 times (10 periods) (at intervals of 100 msec).

Notably, in the case where the microprocessor 30 determines in S134 that the postponed period flag is 1 (Yes), the microprocessor 30 proceeds directly to step S34 by skipping steps S32 and S33; i.e., without performing the comparison of the value of the ΔVs detection timing counter. Accordingly, in the where the postponed period flag is 1 (this flag is set to 1 in step S133 described below), the 100 msec interval of the detection of the voltage change amount ΔVs is extended exceptionally.

In step S34, the microprocessor 30 resets the value of the ΔVs detection timing counter to 0.

In step S35 subsequent to step S34, the microprocessor 30 starts the timer for clocking the time of 200 μsec (wait time TW).

In step S36 subsequent thereto, the microprocessor 30 waits until the 200 μsec timer started in step S35 is up. When 200 μsec (wait time TW) has elapsed and the timer is up (Yes), the microprocessor 30 proceeds to step S131.

In step S131, the microprocessor 30 determines whether or not the transmission of the CAN transmission data Tx to the ECU 100 is being performed (in the middle of CAN transmission). In the case where the microprocessor 30 determines that the present point is not the middle of CAN transmission (No), the microprocessor 30 proceeds to step S132 so as to set the postponed period flag to 0, and then proceeds to step S37 (third timing t3).

In step S37, the microprocessor 30 sends (outputs), through the serial transmission port 33, the instruction command SC (instruction signal) for instructing the detection of the voltage change amount ΔVs to the control section 59 of the sensor element section control circuit 40. Upon completion of the output of the instruction command SC, the microprocessor 30 proceeds to step S38.

In step S38, the microprocessor 30 permits the timer interruption at intervals of 1 msec, and ends this trailing edge interruption routine.

Meanwhile, in the case where the microprocessor 30 determines in step S131 that the present point is the middle of CAN transmission (Yes), the microprocessor 30 proceeds to step S133 so as to set the postponed period flag to 1, and then proceeds to step S38). In this case, since the microprocessor 30 does not perform the processing of step S37 in the period T for which it is determined that the CAN transmission is being performed, the output of the instruction command SC at the third timing t3 is stopped.

In the period T subsequent to the period T in which the output of the instruction command SC was stopped because of the postponed period flag being set to 1, the microprocessor 30 makes a "Yes" determination in step S134, and proceeds to step S34. Accordingly, step S34 and steps subsequent thereto are again executed, and, when it is determined in step S131 that the present point is not in the middle of the CAN transmission (No), the instruction command SC is output in step S37. Thus, the period T in which the instruction command SC is output is postponed.

In the present first modification, the microprocessor 30 which executes the above-mentioned step S131 of determining whether or not the CAN transmission is being performed, immediately before outing the instruction command SC (step S37) corresponds to the pre-output transmission determination means.

The processing of skipping step S37 in the case where the microprocessor 30 makes a "Yes" determination in step S131 corresponds to the output stopping means.

The microprocessor 30 which executes the above-mentioned steps S132 and S133 of setting the postponed period flag to 0 or 1 and the above-mentioned step S134 of determining whether or not the postponed period flag is 1 corresponds to the period postponing output means.

The microprocessor 30 which executes the pre-output transmission determination means, the output stopping means (step S131), and the period postponing output means (steps S132, S133, S134) corresponds to the prevention means.

The CAN protocol controller 35 and the CAN transceiver 80 correspond to the data transmission means for transmitting data (CAN transmission data Tx) to the ECU 100 (external device).

Since the gas sensor control apparatus 1A of the present first modification includes the prevention means (steps S131, S132, S133, S134), in addition to an action and effect similar to those of the embodiment, the following action and effect can be attained. Specifically, it is possible to prevent use of the voltage change amount $\Delta Vs$ or the element resistance Rpvs obtained therefrom, which are affected by the transmission of data because of overlapping between the transmission period TS of data (CAN transmission data Tx) transmitted to the ECU 100 (external device) and a portion of the period TK (detection period) of the operation of detecting the voltage change amount $\Delta Vs$ (response change amount) subsequent to the output of the instruction command SC (instruction signal) at the third timing t3.

Further, in the gas sensor control apparatus 1A of the present first modification, the prevention means includes the pre-output transmission determination means for determining, prior to the output of the instruction command SC (instruction signal) at the third timing t3, whether or not transmission of data is being performed (whether or not the present point is in the middle of CAN transmission) at a point in time (pre-output determination timing) before the third timing t3 (step S131); and the output stopping means (step S131 (the case of Yes) for stopping the output of the instruction command SC at the third timing t3 when it is determined that the data transmission is being performed (in the middle of CAN transmission).

By virtue of the above-described configuration, the voltage change amount $\Delta Vs$ and the element resistance Rpvs are prevented from assuming values affected by the transmission of data, and only a proper value of the element resistance Rpvs is used.

Moreover, in the gas sensor control apparatus 1A of the present first modification, in the case where the output of the instruction command SC at the third timing t3 is stopped, the instruction command SC is output at the third timing t3 in the period T subsequent to the period T in which the output of the instruction command SC was stopped (the period postponing output means: steps S132, S133, S134).

By virtue of this configuration, even when the output of the instruction command SC at the third timing t3 is stopped, it is possible to obtain a proper voltage change amount $\Delta Vs$ by outputting the instruction command SC in the next period T, whereby the element resistance Rpvs can be detected properly and substantially regularly.

Second Modification

Next, the second modification of the above-described embodiment will be described.

A gas sensor control apparatus 1B (see FIG. 7) according to the present second modification has a configuration substantially the same as that of the gas sensor control apparatus 1A according to the first modification. However, as will be described next, the configuration of the prevention means partially differs from that of the first modification. Notably, a description of portions similar to those of the embodiment or the first modification will be omitted or such portions will be described only briefly.

In the present second modification, in addition to the pre-output transmission determination means and the output stopping means, which are similar to those of the first modification, timing postponing output means is provided in place of the period postponing output means of the first modification.

In the case where the output of the instruction command SC (instruction signal) at the third timing t3 is stopped by the output stopping means, the timing postponing output means causes the instruction signal output means to output the instruction command SC at a fourth timing t4 which comes after the third timing t3 within the period T in which the output of the instruction command SC was stopped.

Figure 10A:
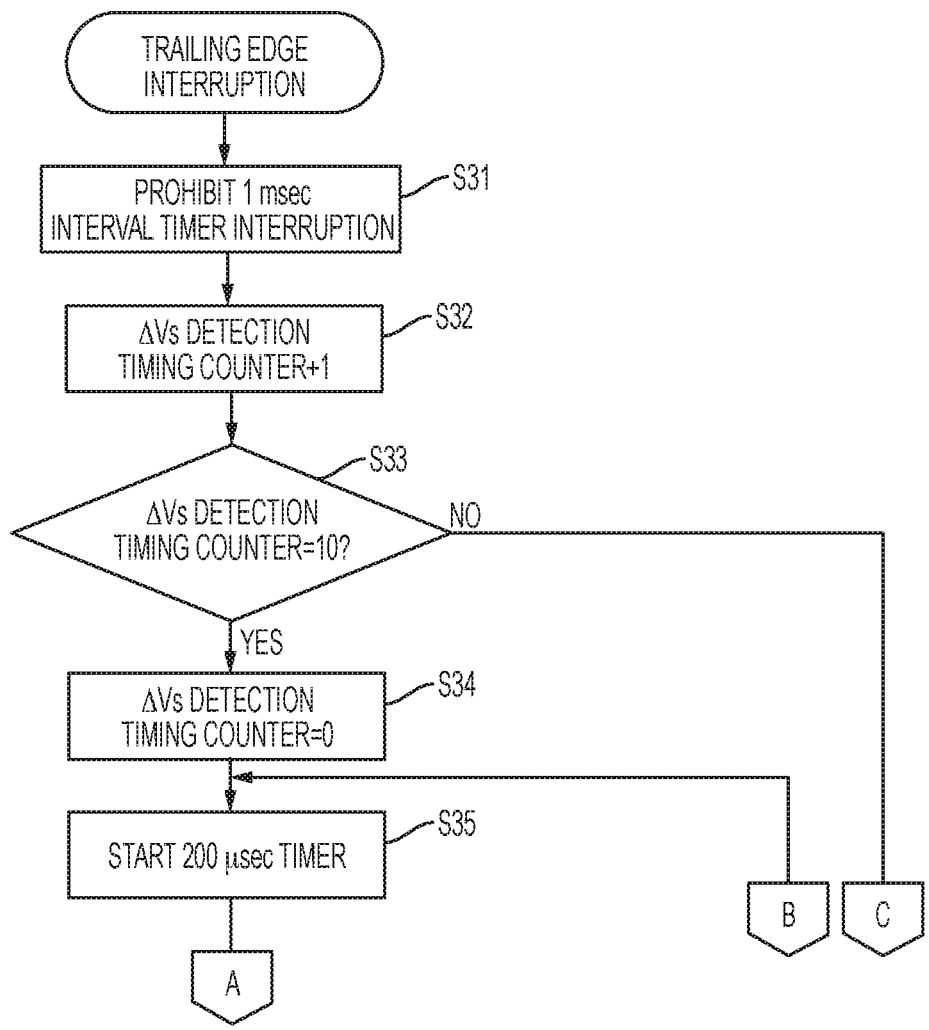
FIGS. 10A and 10B are flowcharts showing the details of a trailing edge interruption routine according to the second modification.
Figure 10B:
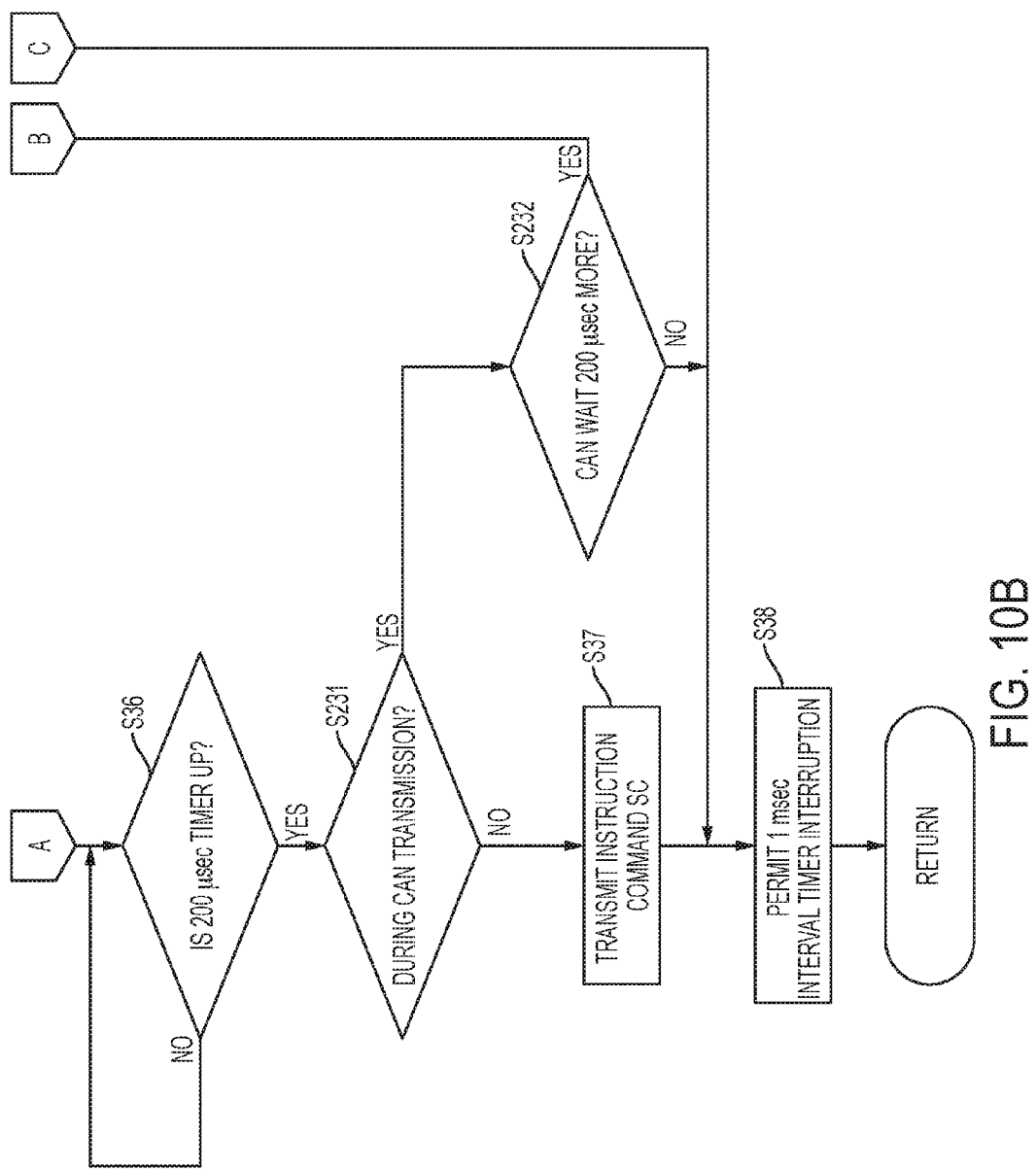

FIGS. 10A and 10B show the trailing edge interruption routine among the processing operations (routines) of the microprocessor 30 of the gas sensor control apparatus 1B according to the present second modification. Notably, the present second modification is identical with the embodiment and the first modification except for the leading edge interruption routine. This trailing edge interruption routine will be described below, in which the difference between the present modification and the embodiment or the first modification will be mainly described.

Figure 5:
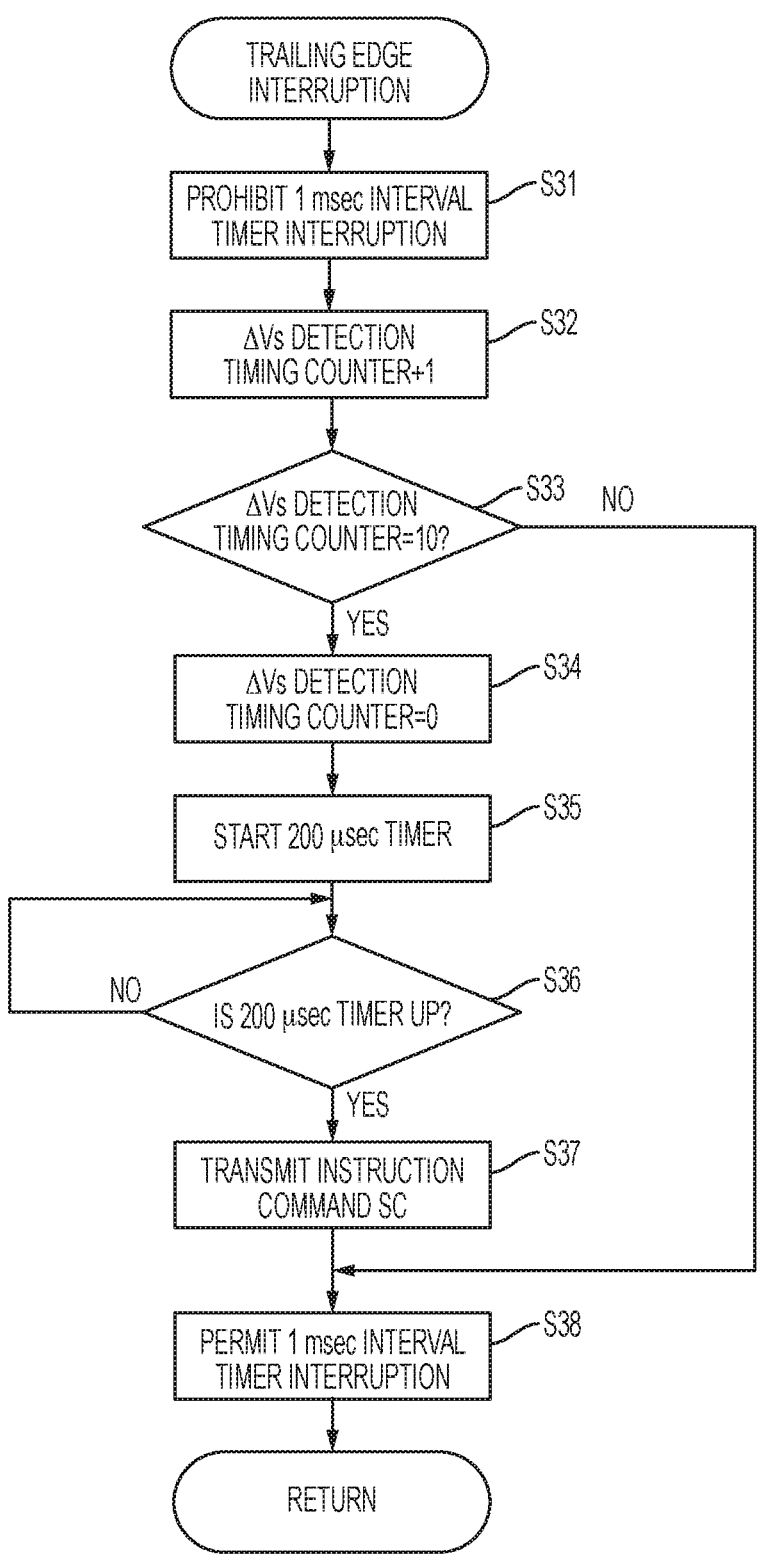
FIG. 5 is a flowchart showing the details of a trailing edge interruption routine.

In the present second modification, the trailing edge interruption routine does not have a step corresponding to step S134 (see FIGS. 9A and 9B) of the trailing edge interruption routine of the first modification, and steps S31 to S34 are the same as those of the trailing edge interruption routine of the embodiment shown in FIG. 5. Accordingly, when the value of the $\Delta Vs$ detection timing counter becomes 10, the microprocessor 30 makes a "Yes" determination in step S33, and proceeds to step S34. Meanwhile, when the microprocessor 30 determines in step S33 that the value of the $\Delta Vs$ detection timing counter is not 10 (No), the microprocessor 30 proceeds to step S38.

Steps S35 and S36 subsequent to step S34 are the same as those of the trailing edge interruption routine of the first modification. When the 200 μsec timer started in step S35 is up, the microprocessor 30 makes a "Yes" determination in step S36, and proceeds to step S231.

In step S231, the microprocessor 30 determines whether or not the transmission of the CAN transmission data Tx is being performed (in the middle of CAN transmission) as in the case of step S131 of the first modification. In the case where the microprocessor 30 determines that the present point is not the middle of CAN transmission (No), the microprocessor 30 proceeds to step S37 (the third timing t3).

In step S37, the microprocessor 30 sends (outputs) the instruction command SC (instruction signal). Subsequently, the microprocessor 30 proceeds to step S38 so as to permit the timer interruption at intervals of 1 msec, and ends this trailing edge interruption routine.

Meanwhile, in the case where the microprocessor 30 determines in step S231 that the present point is in the middle of the CAN transmission (Yes), the microprocessor 30 proceeds to step S232. As described above, the microprocessor 30 stops the output of the instruction command SC at the third timing t3 by skipping step S37.

In step S232, in consideration of the relation with the maximum value $TB_{1-2max}$ (=9.5 msec) of the pulse width PSW, the microprocessor 30 determines whether or not the output of the instruction command SC can be delayed for 200 μsec more within the same period T in which the output of the instruction command SC was stopped once. In the case where the output of the instruction command SC cannot be delayed for 200 μsec due to the relation with the maximum value $TB_{1-2max}$ (No), the microprocessor 30 proceeds to step S38, whereby the output of the instruction command SC in this period T is stopped.

Meanwhile, in the case where the output of the instruction command SC can be delayed for 200 μsec (Yes), the microprocessor 30 returns to step S35 so as to again start the 200 μsec timer, waits for 200 μsec in step S36, and again determines in step S231 whether or not the present point is in the middle of the CAN transmission. In the case where the microprocessor 30 determines that the present point is not in the middle of the CAN transmission (No), the microprocessor 30 proceeds to step S37 (the fourth timing t4), and outputs the instruction command SC. Meanwhile, in the case where the microprocessor 30 determines that the present point is in the middle of the CAN transmission (Yes), the microprocessor 30 again proceeds to step S232 so as to determine whether or not the output of the instruction command SC can be delayed for 200 μsec further.

By virtue of this configuration, the instruction command SC can be output at the fourth timing t4 after the third timing t3 within the period T in which the output of the instruction command SC at the third timing t3 was stopped.

In the present second modification, the microprocessor 30 which executes the above-mentioned step S231 of determining whether or not the present point is in the middle of the CAN transmission corresponds to the pre-output transmission determination means.

The processing of skipping step S37 in the case where the microprocessor 30 makes a "Yes" determination in step S231 corresponds to the output stopping means.

The microprocessor 30 which executes the above-mentioned steps S231 and S232 and returns to the above-mentioned step S35 corresponds to the timing postponing output means.

The microprocessor 30 which executes the pre-output transmission determination means, the output stopping means (step S231), and the timing postponing output means (steps S231, S232) corresponds to the prevention means.

The gas sensor control apparatus 1B of the present second modification includes the pre-output transmission determination means and the output stopping means (step S231). In addition, when the output of the instruction command SC at the third timing t3 is stopped, the gas sensor control apparatus 1B outputs the instruction command SC at the fourth timing t4 after the third timing t3 in the period T in which the output of the instruction command SC was stopped. (the timing postponing output means: step S231, S232).

By virtue of the above-described configuration, even in the case where the output of the instruction command SC at the third timing t3 is stopped once, it is possible to obtain the voltage change amount ΔVs by outputting the instruction command SC at the fourth timing t4 after the timing t3, whereby the element resistance Rpvs can be detected substantially regularly.

In the gas sensor control apparatus 1B of the present second modification, the microprocessor 30 determines at a point in time (postponement determination timing) before the fourth timing t4 whether or not the present point in time is in the middle of the CAN transmission, and permits the output of the instruction command SC at the fourth timing t4 (step S231). By virtue of this configuration, it is possible to obtain a proper voltage change amount ΔVs and detect a proper element resistance Rpvs regularly.

Third Modification

Next, the third modification of the above-described embodiment will be described.

A gas sensor control apparatus 1C (see FIG. 7) according to the present third modification also has a configuration substantially the same as that of the gas sensor control apparatus 1A according to the first modification. However, as will be described next, the configuration of the prevention means partially differs from that of the first modification. Therefore, as in the case of the second modification, a description of portions similar to those of the embodiment or the first modification will be omitted or such portions will be described only briefly.

In the present third modification, in place of the pre-output transmission determination means of the first modification, an intra-period transmission determination means is provided for determining at the first timing t1 in the period T to which the third timing t3 belongs whether or not the transmission of the CAN transmission data Tx (CAN transmission) is performed in this period T. Also, the gas sensor control apparatus 1C of the present modification has an output stopping means and a period postponing output means as in the case of the gas sensor control apparatus 1A of the first modification.

Figure 11:
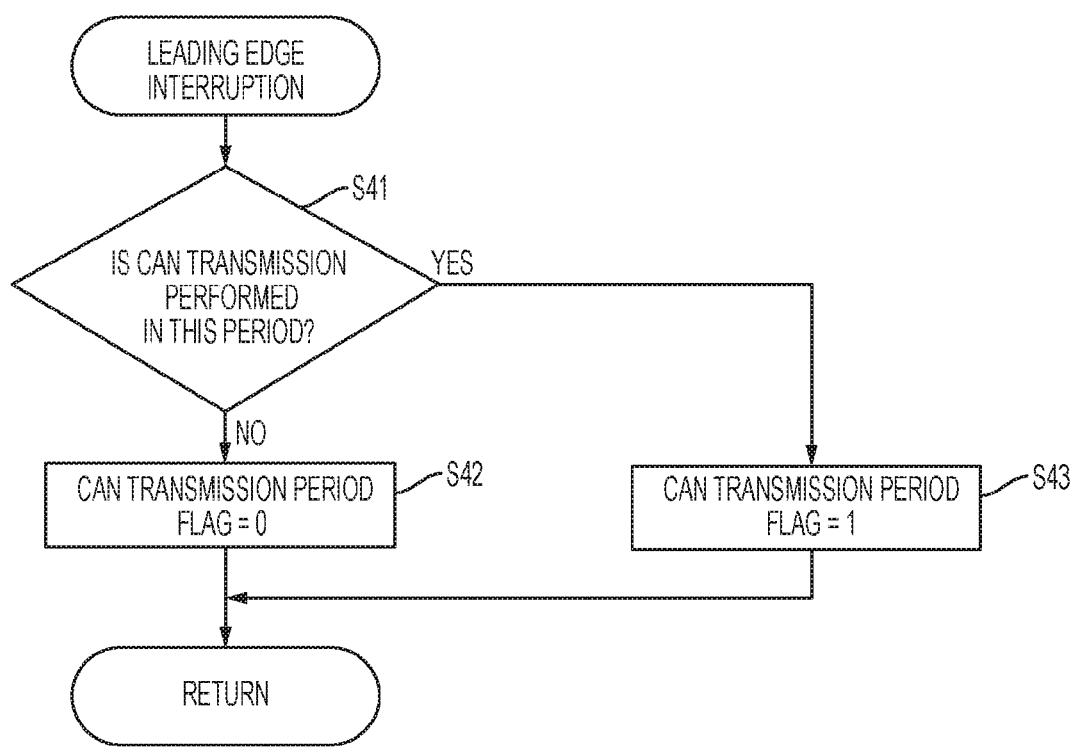
FIG. 11 is a flowchart showing the details of a leading edge interruption routine according to the third modification.
Figure 12A:
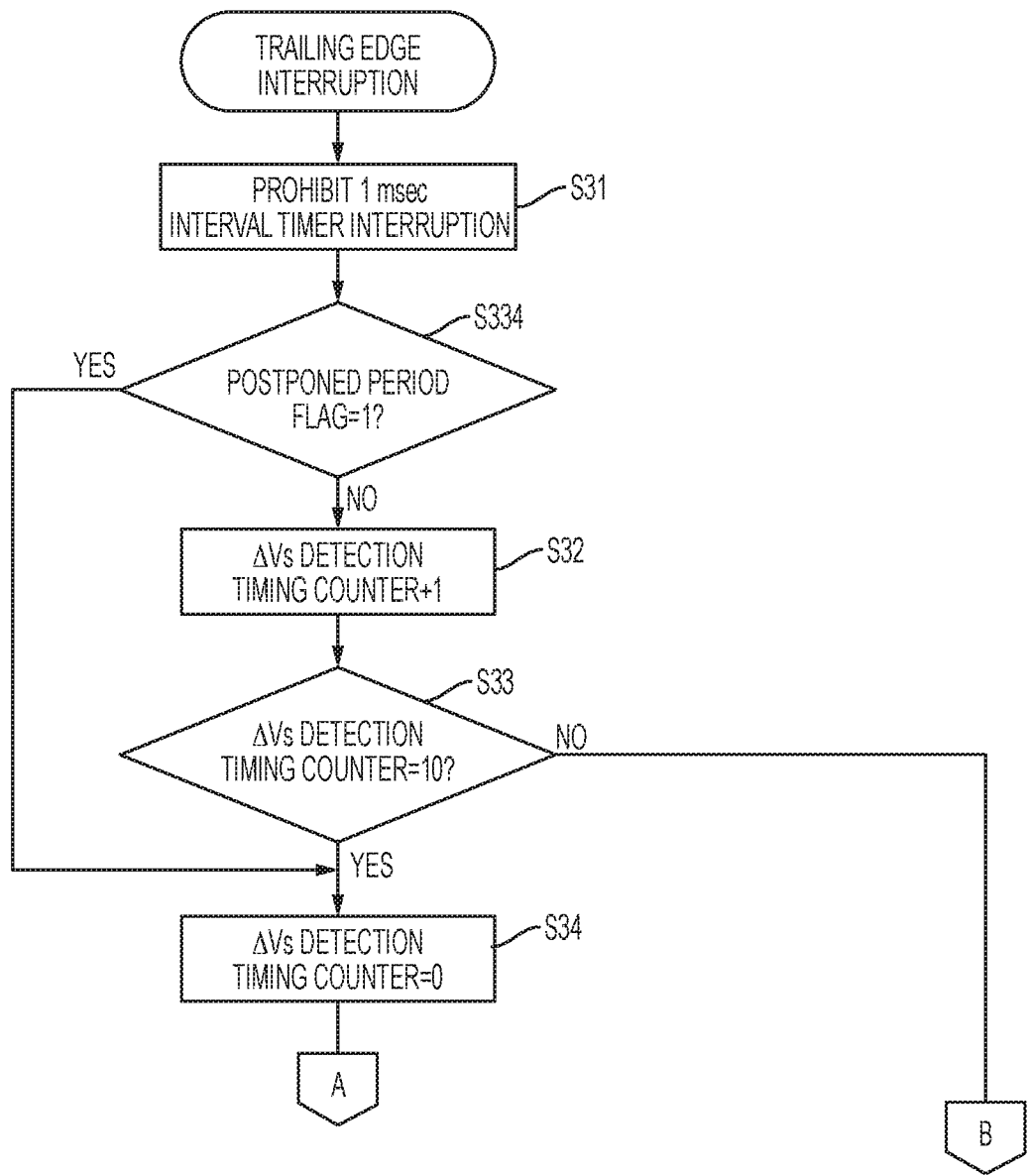
FIGS. 12A and 12B are flowcharts showing the details of a trailing edge interruption routine according to the third modification.
Figure 12B:
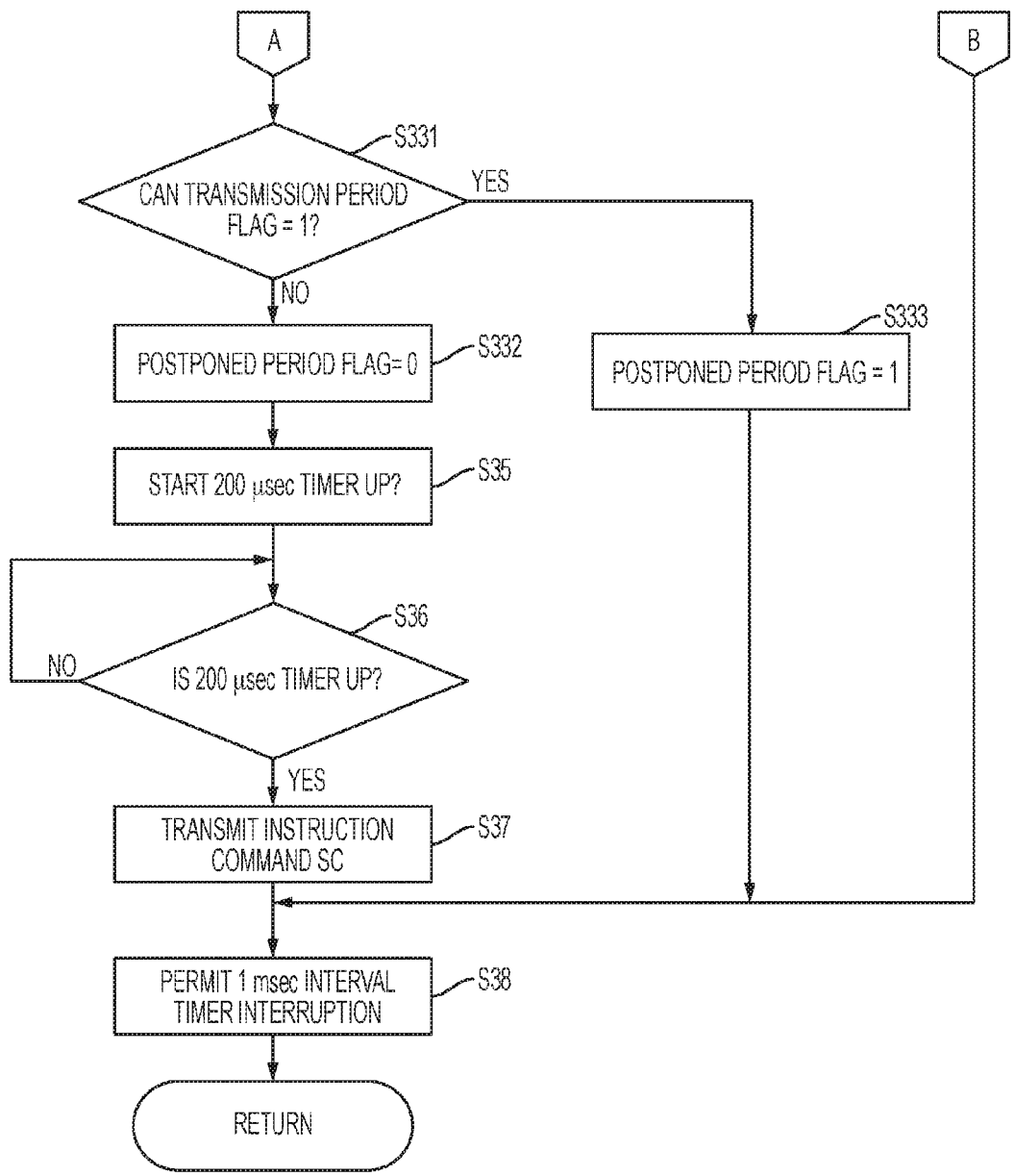

FIG. 11 shows the leading edge interruption routine among the processing operations (routines) of the microprocessor 30 of the gas sensor control apparatus 1C according to the present third modification. FIGS. 12A and 12B show the trailing edge interruption routine. Unlike the embodiment and the first and second modifications, not only the interruption generated at the trailing edge of each PWM pulse PS, but also the interruption generated at the leading edge of each PWM pulse PS is used in the present third modification. First, the leading edge interruption routine will be described with reference to the flowchart of FIG. 11.

The leading edge interruption is generated by the timer counter which functions in combination with the PWM output port 34 every time the leading edge PSU (the first timing t1) of each PWM pulse PS arrives (see FIG. 8). In the present third modification, for generation of the leading edge interruption, in addition to the trailing edge interruption and the 1 msec interval timer interruption, the leading edge interruption is permitted in a step of the unillustrated main processing which corresponds to step S5 (see FIG. 3) of the embodiment.

In the present third modification, every time the leading edge interruption is generated, the microprocessor 30 determines in step S41 (the first timing t1) whether or not the transmission of the CAN transmission data Tx to the ECU 100 (CAN transmission) is performed within the period T starting from this first timing t1. For example, in the case where the CAN transmission is started in synchronism with the first timing t1, such determination is possible.

In the case where the microprocessor 30 determines in step S41 that the CAN transmission is not performed within the present period T (No), the microprocessor 30 proceeds to step S42 so as to set a CAN transmission period flag to 0, and ends this leading edge interruption routine. Meanwhile, in the case where the microprocessor 30 determines in step S41 that the CAN transmission is performed within the present period T (Yes), the microprocessor 30 proceeds to step S43 so as to set the CAN transmission period flag to 1, and ends the leading edge interruption routine.

Next, the trailing edge interruption routine will be described with reference to the flowcharts of FIGS. 12A and 12B.

Steps S31, S334, S32, S33, and S34 of the trailing edge interruption routine of the present third modification are identical with those of the trailing edge interruption routine of the first modification (see FIGS. 9A and 9B). In step S334 (identical with step S134 of the first modification) subsequent to step S31, the microprocessor 30 determines whether or not the postponed period flag is 1. In the case where the postponed period flag is 0 (No in step S334), when the value of the ΔVs detection timing counter becomes 10, the microprocessor 30 makes a "Yes" determination in step S33, and proceeds to step S34. Meanwhile, the microprocessor 30 determines in step S33 that the value of the ΔVs detection timing counter is not 10 (No), the microprocessor 30 proceeds to step S38. In the case where the postponed period flag is 1 (Yes in step S334), the microprocessor 30 proceeds to step S34 by skipping steps S32 and S33.

In step S331 subsequent to step S34, the microprocessor 30 determines whether or not the CAN transmission period flag set in step S42 or step S43 of the leading edge interruption routine (see FIG. 11) is 1. As described above, the value of the CAN transmission period flag is updated to 0 or 1 every time the leading edge interruption is generated. Namely, the value of the CAN transmission period flag is updated for each period T. Meanwhile, the determination of step S331 as to whether the value of the CAN transmission period flag is 1 is performed only for periods T in which the voltage change amount ΔVs is detected; namely, only when the postponed period flag is 1 and when the microprocessor 30 determines in step S33 that the value of the ΔVs detection timing counter becomes 10 when the postponed period flag is 0.

In the case where the microprocessor 30 determines in step S331 that the CAN transmission period flag is 0 (No), the microprocessor 30 proceeds to step S332 so as to set the postponed period flag to 0, and proceeds to step S35.

Steps S35 and S36 are the same as those of the trailing edge interruption routine of the first modification. When the 200 μsec timer started in step S35 is up, the microprocessor 30 makes a "Yes" determination in step S36, and proceeds to step S37 (the third timing t3).

In step S37, the microprocessor 30 sends (outputs) the instruction command SC (instruction signal), and then proceeds to step S38 so as to permit the timer interruption at intervals of 1 msec, and ends this trailing edge interruption routine.

Meanwhile, in the case where the microprocessor 30 determines in step S331 that the CAN transmission period flag is 1 (Yes), the microprocessor 30 proceeds to step S333 so as to set the postponed period flag to 1, and then proceeds to step S38. Since the microprocessor 30 does not pass through step S37 in the period T determined to have CAN transmission, the output of the instruction command SC at the third timing t3 is stopped.

As a result of the postponed period flag being set to 1, in the period T subsequent to the period T in which the output of the instruction command SC was stopped, the microprocessor 30 makes a "Yes" determination in step S334, and proceeds to step S34. Accordingly, step S34 and steps subsequent thereto are executed again, and the instruction command SC is output in step S37 if the CAN transmission period flag is 0 (No in step S331). As a result, the period T in which the instruction command SC is output is postponed.

In the present third modification, the microprocessor 30 which executes the above-mentioned step S41 of determining whether or not the CAN transmission is performed and the above-mentioned steps S42 and S43 of setting the CAN transmission period flag to 0 or 1 corresponds to the intra-period transmission determination means.

Of the processing of the microprocessor 30 which executes the above-mentioned step S331 of determining whether or not the CAN transmission period flag is 1, the processing of skipping the above-mentioned step S37 when the result of the determination becomes "Yes" corresponds to the output stopping means.

The microprocessor 30 which executes the above-mentioned steps S332 and S333 of setting the postponed period flag to 0 or 1 and executes the above-mentioned step S334 of determining whether or not the postponed period flag is 1 corresponds to the period postponing output means.

The microprocessor 30 which executes the intra-transmission determination means (steps S41, S42, S43), the output stopping means (step S331), and the period postponing output means (steps S332, S333, S334) corresponds to the prevention means.

As described above, the gas sensor control apparatus 1C of the present third modification includes the intra-transmission determination means (steps S41, S42, S43) for determining at the first timing t1 whether or not the CAN transmission is performed within the period T starting from this first timing; and the output stopping means (step S331 (the case of Yes)) for stopping the output of the instruction command SC at the third timing t3.

By virtue of this configuration, the voltage change amount ΔVs and the element resistance Rpvs are prevented from assuming values affected by the CAN transmission, and only a proper value of the element resistance Rpvs is used.

Moreover, like the gas sensor control apparatus 1A of the first modification, the gas sensor control apparatus 1C of the present third modification includes the period postponing output means (steps S332, S333, S334) for outputting the instruction command SC at the third timing t3 in the period T subsequent to the period T in which the output of the instruction command SC was stopped.

By virtue of this configuration, even when the output of the instruction command SC at the third timing t3 is stopped once, it is possible to obtain a proper voltage change amount ΔVs by outputting the instruction command SC in the next period T, whereby the element resistance Rpvs can be detected properly and substantially regularly.

Fourth Modification

Next, the fourth modification of the above-described embodiment will be described.

A gas sensor control apparatus 1D (see FIG. 7) according to the present fourth modification has substantially the same configuration as that of the gas sensor control apparatus 1A according to the first modification. However, as will be described next, the configuration of the prevention means differs from that of the first modification. Therefore, as in the case of the second and third modifications, a description of portions similar to those of the embodiment or the first modification will be omitted or such portions will be described only briefly.

In the present fourth modification, in place of the pre-output transmission determination means of the first modification, pre-detection transmission determination means is provided so as to determine whether or not the CAN transmission is being performed at a point in time (pre-detection determination timing) before the detection operation period TK (detection period). Also, the output stopping means of the first through third modifications is not provided, and the instruction command SC is output at the third timing t3 as is. Meanwhile, use prohibition means is provided for preventing use of the voltage change amount ΔVs (response change amount) detected in the detection operation period TK or the element resistance Rpvs detected therefrom when the pre-detection transmission determination means determines that the CAN transmission is being performed.

Furthermore, in the present fourth modification, re-output means is provided which operates, when the pre-detection transmission determination means determines that the CAN transmission is being performed, so as to output the instruction command SC again in the period T subsequent to the period T in which the instruction command SC was output.

Figure 13A:
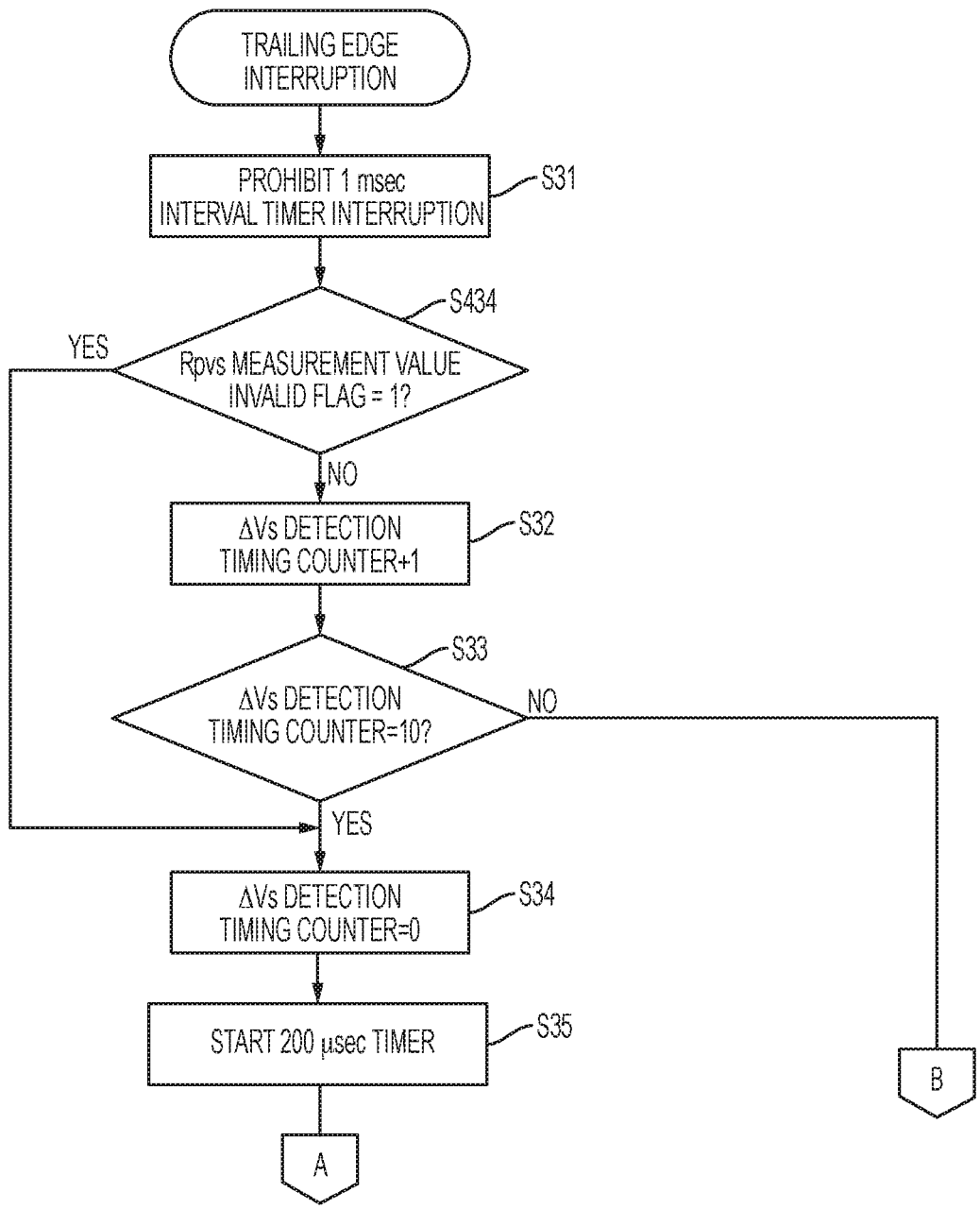
FIGS. 13A and 13B are flowcharts showing the details of a trailing edge interruption routine according to the fourth modification.
Figure 13B:
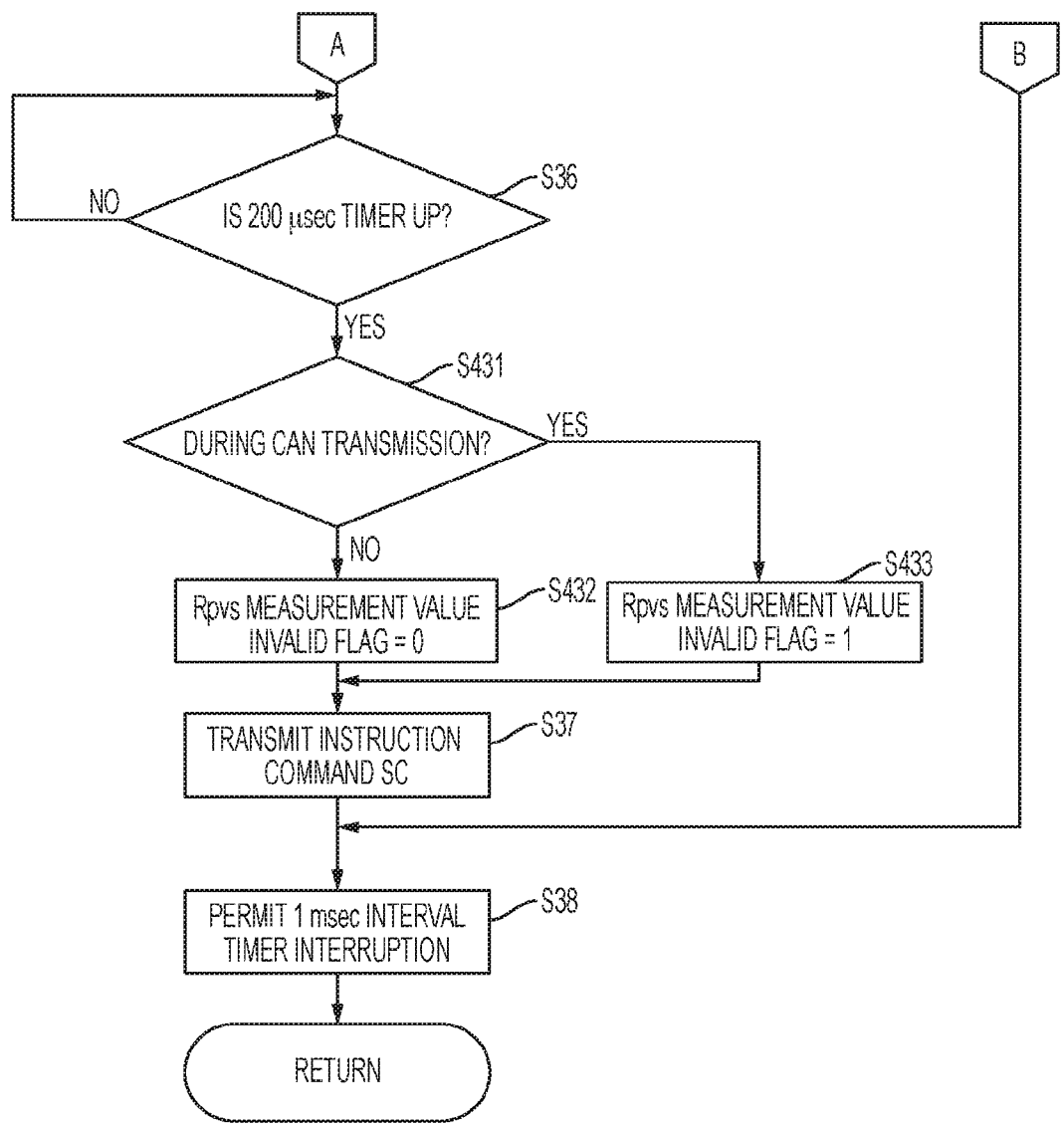

FIGS. 13A and 13B show the trailing edge interruption routine among the processing operations (routines) of the microprocessor 30 of the gas sensor control apparatus 1D according to the present fourth modification. This trailing edge interruption routine will be described below, and in particular, the difference between the present modification and the first modification.

Steps S31, S434, S32, S33, and S34 of the present fourth modification are basically the same as those of the first modification (see FIGS. 9A and 9B). However, the present fourth modification differs from the first modification in the following point. In the first modification, in step S134 subsequent to step S31, a determination is made as to whether the postponed period flag is 1. In contrast, in the present fourth modification, in step S434 subsequent to step S31, a determination is made as to whether an Rpvs measurement value invalid flag to be described later is 1. In the case where the Rpvs measurement value invalid flag is 0 (No in step S434), when the value of the ΔVs detection timing counter becomes 10, the microprocessor 30 makes a "Yes" determination in step S33, and proceeds to step S34. Meanwhile, in the case where the microprocessor 30 determines in step S33 that the value of the ΔVs detection timing counter is not 10 (No), the microprocessor 30 proceeds to step S38. Also, in the case where the Rpvs measurement value invalid flag is 1 (Yes in step S434), the microprocessor 30 proceeds to step S34 while skipping steps S32 and S33.

Also, steps S35 and S36 subsequent to step S34 are the same as those of the first modification. When the 200 μsec timer started in step S35 is up, the microprocessor 30 makes a "Yes" determination in step S36, and proceeds to step S431.

In step S431, as in the case of step S131 of the first modification, the microprocessor 30 determines whether or not the CAN transmission is being performed. In the case where the microprocessor 30 determines that the CAN transmission is not being performed (No), the microprocessor 30 proceeds to step S432 so as to set the Rpvs measurement value invalid flag to 0, and then proceeds to step S37 (third timing t3). Meanwhile, in the case where the microprocessor 30 determines that the CAN transmission is being performed (Yes), the microprocessor 30 proceeds to step S433 so as to set the Rpvs measurement value invalid flag to 1, and then proceeds to step S37 (also, third timing t3).

In step S37, the microprocessor 30 sends (outputs) the instruction command SC (instruction signal), and then proceeds to step S38 so as to permit the timer interruption at intervals of 1 msec, and ends this trailing edge interruption routine.

Notably, in the case where the Rpvs measurement value invalid flag is set to 1 in step S433, the microprocessor 30 does not perform the sampling of the voltage change amount ΔVs and the calculation of the element resistance Rpvs in a 1 msec interval timer interruption routine (see FIGS. 14A and 14B) to be described next. Also, as a result of the Rpvs measurement value invalid flag being set to 1, in the next the period T, the microprocessor 30 makes a "Yes" determination in step S434, and proceeds to step S34. As a result, step S34 and steps subsequent thereto are executed again, whereby the instruction command SC is output again.

Next, the 1 msec interval timer interruption routine of the gas sensor control apparatus 1D according to the present fourth modification will be described with reference to the flowcharts of FIGS. 14A and 14B.

Figure 14A:
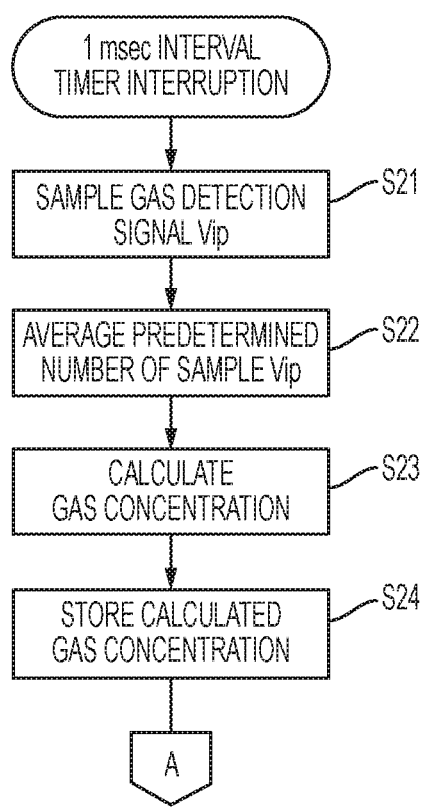
FIGS. 14A and 14B are flowcharts showing the details of a timer interruption routine according to the fourth and fifth modifications.
Figure 14B:
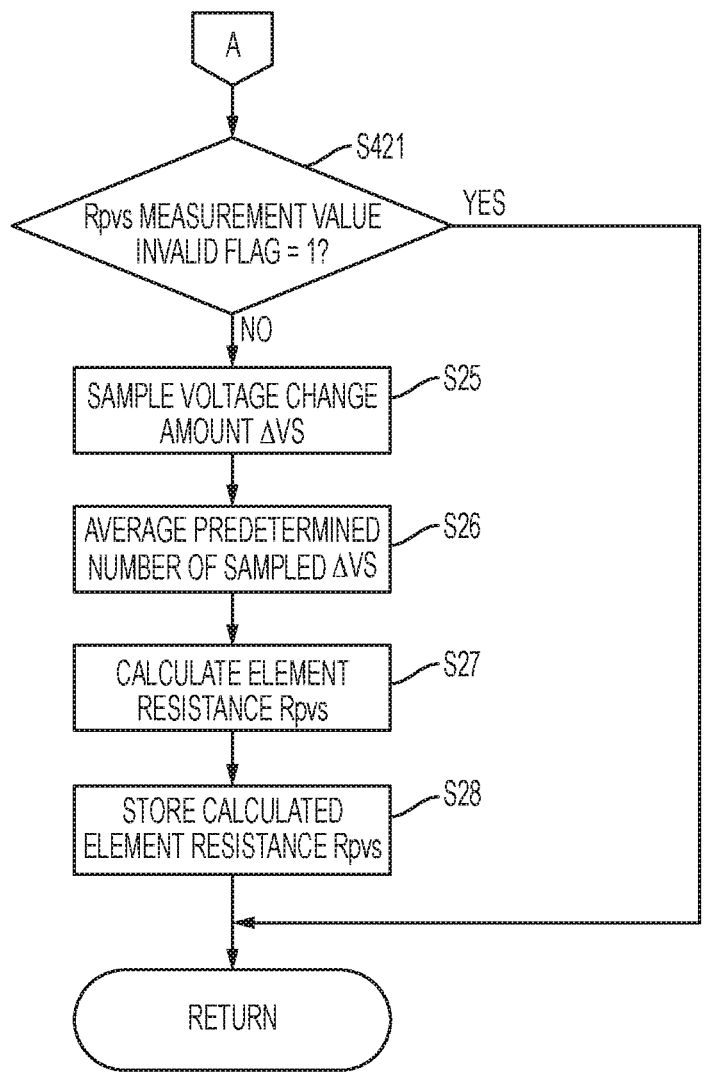

In FIGS. 14A and 14B, steps S21 to S24 are identical with those of the 1 msec interval timer interruption routine of the embodiment (see FIG. 4). In these steps, the microprocessor 30 calculates the gas concentration on the basis of the sampled gas detection signal Vip, and stores the calculated gas concentration in a predetermined memory.

In step S421 subsequent to step S24, the microprocessor 30 determines whether or not the Rpvs measurement value invalid flag set in step S432 or step S433 of FIG. 13B is 1.

In the case where the microprocessor 30 determines in step S421 that the Rpvs measurement value invalid flag is 0 (No), the microprocessor 30 proceeds to step S25. Steps S25 to S28 are identical with those of the 1 msec interval timer interruption routine of the embodiment. In these steps, the microprocessor 30 calculates the element resistance Rpvs on the basis of the sampled voltage change amount ΔVs, and stores the calculated element resistance Rpvs in the predetermined memory. After that, the microprocessor 30 ends this 1 msec timer interruption routine.

Meanwhile, in the case where the microprocessor 30 determines in step S421 that the Rpvs measurement value invalid flag is 1 (Yes), the microprocessor 30 ends the 1 msec timer interruption routine without performing the above-mentioned steps S25 to S28 of sampling the voltage change amount ΔVs and calculating the element resistance Rpvs.

In the present fourth modification, the microprocessor 30 which executes the above-mentioned step S431 of determining at the timing before the detection operation period TK whether or not the CAN transmission is being performed corresponds to the pre-detection transmission determination means.

The microprocessor 30 which executes the above-mentioned steps S432 and S433 of setting the Rpvs measurement value invalid flag to 0 or 1 and the above-mentioned step S421 of determining whether or not the Rpvs measurement value invalid flag is 1 in the 1 msec interval timer interruption routine corresponds to the use prohibition means.

The microprocessor 30 which executes the above-mentioned steps S432 and S433 of setting the Rpvs measurement value invalid flag to 0 or 1 and the above-mentioned step S434 of determining whether or not the Rpvs measurement value invalid flag is 1 corresponds to the re-output means.

The microprocessor 30 which executes the pre-detection transmission determination means (step S431), the use prohibition means (steps S432, S433, S434 and step S421), and the re-output means (steps S432, S433, S434) corresponds to the prevention means.

As described above, the gas sensor control apparatus 1D of the present fourth modification includes the pre-detection transmission determination means (step S431). In the case where the CAN transmission is being performed at the pre-detection determination timing (the third timing t3) before the detection operation period TK (detection period), use of the voltage change amount ΔVs detected in the detection operation period TK is prohibited by the use prohibition means (steps S432, S433 and step S421), so that the value of the element resistance Rpvs is not updated (measured).

Thus, the voltage change amount ΔVs and the element resistance Rpvs affected by the CAN transmission are not used, and only a proper value of the element resistance Rpvs is used.

Moreover, in the gas sensor control apparatus 1D of the present fourth modification, in the case where the pre-detection transmission determination means determines that the CAN transmission is being performed, the instruction command SC is output again in the period T subsequent to the period T in which the instruction command SC was output (the re-output means: steps S432, S433, S434).

By virtue of this configuration, it becomes possible to prevent use of the voltage change amount ΔVs or the element resistance Rpvs obtained when the detection operation period TK and the data transmission period TS overlap each other. In addition, it becomes possible to output the instruction command SC again in the next period T so as to obtain the voltage change amount ΔVs, to thereby detect the element resistance Rpvs. Thus, the element resistance Rpvs can be detected substantially regularly.

Fifth Modification

Next, the fifth modification of the above-described embodiment will be described.

A gas sensor control apparatus 1E (see FIG. 7) according to the present fifth modification has substantially the same configuration as that of the gas sensor control apparatus 1D according to the fourth modification. However, the configuration of the prevention means differs from that of the fourth modification in that overlap determination means, which will be described next, is provided in place of the pre-detection transmission determination means of the fourth modification. As set forth below, a description of portions similar to those of the fourth modification will be omitted or such portions will be described only briefly.

In the present fifth modification, the output stopping means is not provided as in the case of the fourth modification, and the instruction command SC is output at the third timing t3 as is. However, in place of the pre-detection transmission determination means of the fourth modification, overlap determination means is provided so as to determine whether or not at least a portion of the detection operation period TK (detection period) subsequent to the output of the instruction command SC at the third timing t3 has actually overlapped with the transmission period TS of data (the CAN transmission data Tx).

Further, use prohibition means is provided which operates, when the overlap determination means determines that overlapping has occurred, so as to prohibit use of the voltage change amount ΔVs (response change amount) detected in the detection operation period TK or the element resistance Rpvs detected therefrom.

Further, in the present fifth modification, re-output means is provided which operates, when the overlap determination means determines that overlapping has occurred, so as to output the instruction command SC again in the period T subsequent to the period T in which the instruction command SC was output.

Figure 15A:
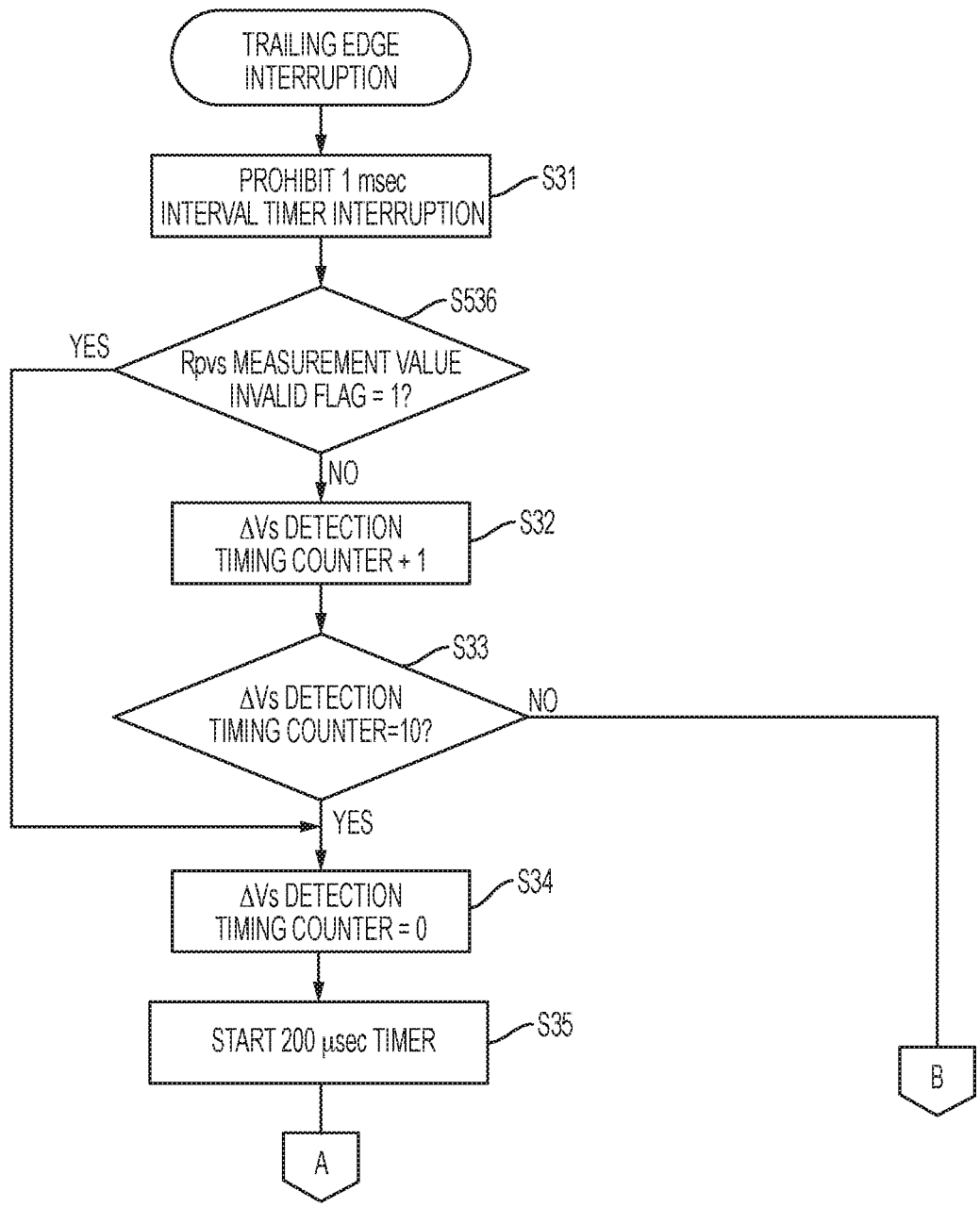
FIGS. 15A and 15B are flowcharts showing the details of a trailing edge interruption routine according to the fifth modification.
Figure 15B:
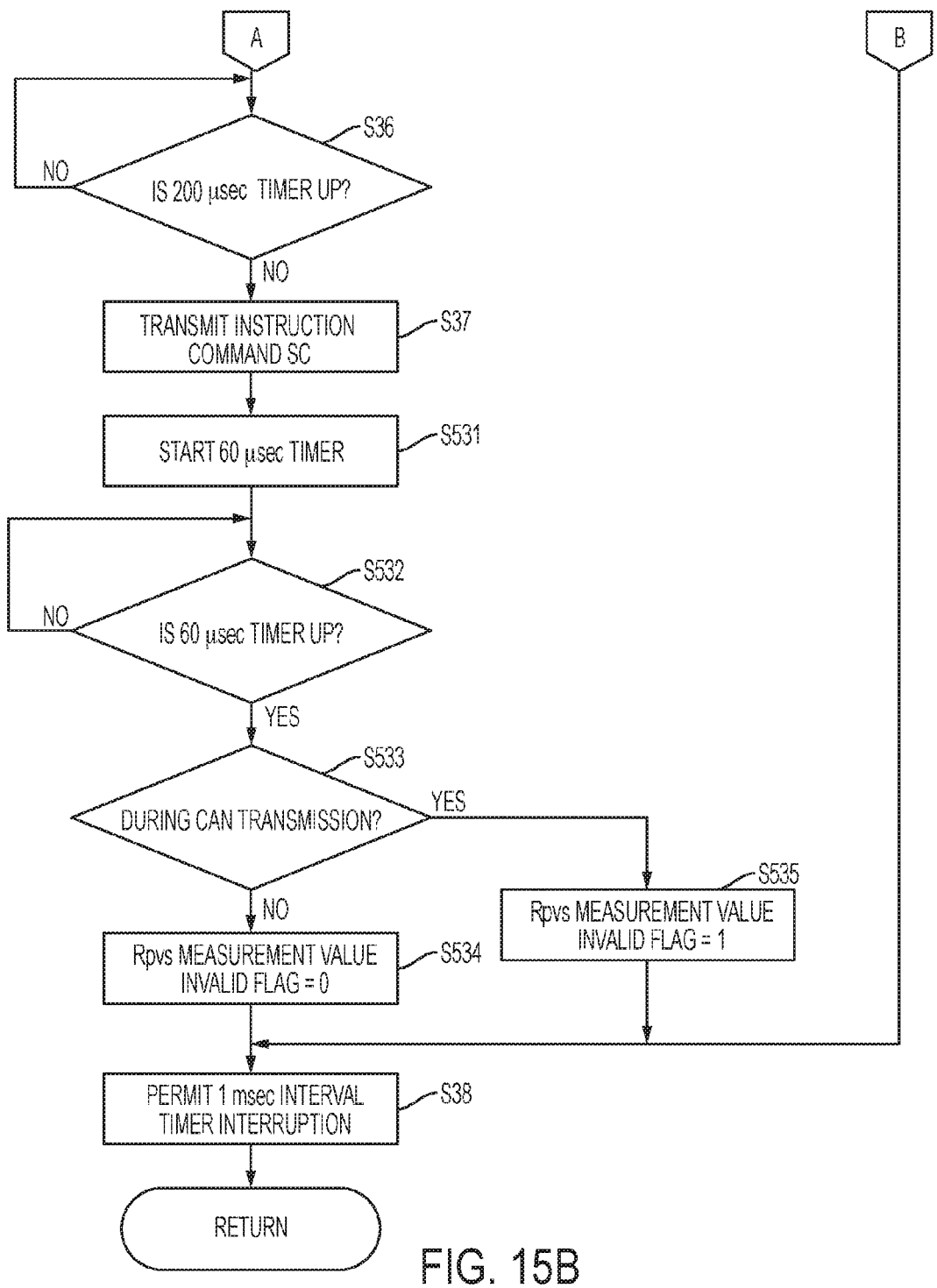

FIGS. 15A and 15B show the trailing edge interruption routine among the processing operations (routines) of the microprocessor 30 of the gas sensor control apparatus 1E according to the present fifth modification. This trailing edge interruption routine will be described below, and in particular, the difference between the present fifth modification and the fourth modification. Further, the present fifth modification also includes the same 1 msec interval timer interruption routine (see FIGS. 14A and 14B) as that of the fourth modification. Notably, the description of this routine will not be repeated.

Steps S31, S536, S32, S33, and S34 of the present fifth modification are the same as those of the fourth modification (see FIGS. 13A and 13B). In step S536 (which is the same as step S434 of the fourth modification) subsequent to step S31, a determination is made as to whether the Rpvs measurement value invalid flag is 1. In the case where the Rpvs measurement value invalid flag is 0 (No in step S536), when the value of the ΔVs detection timing counter becomes 10, the microprocessor 30 makes a "Yes" determination in step S33, and proceeds to step S34. Meanwhile, in the case where the microprocessor 30 determines in step S33 that the value of the ΔVs detection timing counter is not 10 (No), the microprocessor 30 proceeds to step S38. Also, in the case where the Rpvs measurement value invalid flag is 1 (Yes in step S536), the microprocessor 30 proceeds to step S34 while skipping steps S32 and S33.

Also, steps S35 and S36 subsequent to step S34 are the same as those of the fourth modification. When the 200 μsec timer started in step S35 is up, the microprocessor 30 makes a "Yes" determination in step S36, and proceeds to step S37 (the third timing t3).

In step S37, the microprocessor 30 sends (outputs) the instruction command SC (instruction signal). When the output of the instruction command SC is completed, the microprocessor 30 proceeds to step S531.

In step S531, the microprocessor 30 starts a timer which clocks a time of 60 μec.

In step S532 subsequent thereto, the microprocessor 30 waits until the 60 μsec timer started in step S531 is up. When 60 μsec has elapsed and the timer is up (Yes), the microprocessor 30 proceeds to step S533. Notably, the 60 μsec timer started in step S531 is set such that the timing at which the microprocessor 30 proceeds to this step S533 becomes a timing within the period TK of the operation of detecting the voltage change amount ΔVs (detection period).

In step S533, the microprocessor 30 determines at the timing in the detection operation period TK (detection period) whether or not the CAN transmission is being performed. Through this determination, the microprocessor 30 determines whether or not the detection operation period TK (detection period) and the transmission period TS has actually overlapped each other. In the case where the microprocessor 30 determines that the CAN transmission is not being performed (No), the microprocessor 30 proceeds to step S534 so as to set the Rpvs measurement value invalid flag to 0, and then proceeds to step S38. Meanwhile, in the case where the microprocessor 30 determines that the CAN transmission is being performed (Yes), the microprocessor 30 proceeds to step S535 so as to set the Rpvs measurement value invalid flag to 1, and then proceeds to step S38.

After permitting the timer interruption at 1 msec intervals in step S38, the microprocessor 30 ends this trailing edge interruption routine.

Notably, in the case where the Rpvs measurement value invalid flag is set to 1 in step S535, the microprocessor 30 makes a "Yes" determination in step S421 in the same 1 msec interval timer interruption routine as that of the fourth modification (see FIGS. 14A and 14B). Therefore, the sampling of the voltage change amount ΔVs and the calculation of the element resistance Rpvs are not carried out. Also, as a result of the Rpvs measurement value invalid flag being set to 1, in the next the period T, the microprocessor 30 makes a "Yes" determination in step S536, and proceeds to step S34. As a result, step S34 and steps subsequent thereto are executed again, whereby the instruction command SC is output again.

In the present fifth modification, the microprocessor 30 which executes the above-mentioned steps S531 and S532 of waiting for the elapse of 60 μsec after the output of the instruction command SC and the above-mentioned step S533 of determining at the timing in the detection operation period TK (detection period) whether or not the CAN transmission is being performed corresponds to the overlap determination means.

The microprocessor 30 which executes the above-mentioned steps S534 and S535 of setting the Rpvs measurement value invalid flag to 0 or 1 and the above-mentioned step S421 of determining whether or not the Rpvs measurement value invalid flag is 1 in the 1 msec interval timer interruption routine corresponds to the use prohibition means.

The microprocessor 30 which executes the above-mentioned steps S534 and S535 of setting the Rpvs measurement value invalid flag to 0 or 1 and the above-mentioned step S536 of determining whether or not the Rpvs measurement value invalid flag is 1 corresponds to the re-output means.

The microprocessor 30 which executes the overlap determination means (steps S531 to S533), the use prohibition means (steps S534, S535 and step S421), and the re-output means (steps S534, S536, S536) corresponds to the prevention means.

As described above, in the gas sensor control apparatus 1E of the present fifth modification, the overlap determination means (steps S531 to S533) determines whether or not at least a portion of the detection operation period TK (detection period) subsequent to the output of the instruction command SC at the third timing t3 has actually overlapped with the transmission period TS of data (the CAN transmission data Tx). When the detection operation period TK is determined to have overlapped with the transmission period TS, use of the voltage change amount ΔVs detected in the detection operation period TK and the element resistance Rpvs based thereon is prohibited (the use prohibition means: steps S534, S535 and step S421) (see FIGS. 14A and 14B).

Thus, the voltage change amount ΔVs and the element resistance Rpvs affected by the CAN transmission are not used, and only a proper value of the element resistance Rpvs is used.

Moreover, in the gas sensor control apparatus 1E of the present fifth modification, in the case where the overlap determination means (steps S531 to S533) determines that overlapping has occurred, the instruction command SC is output again in the period T subsequent to the period T in which the instruction command SC was output (the re-output means: steps S534, S535, S536).

By virtue of this configuration, it becomes possible to prevent use of the voltage change amount ΔVs and the element resistance Rpvs obtained when the detection operation period TK and the data transmission period TS overlap each other. In addition, it becomes possible to output the instruction command SC again in the next period T so as to obtain a proper voltage change amount ΔVs. Thus, a proper element resistance Rpvs can be detected substantially regularly.

In the above, the gas sensor control apparatus of the present invention has been described on the basis of the gas sensor control apparatus 1 of the gas sensor 2 (air-fuel ratio sensor) according to the embodiment and the gas sensor control apparatuses 1A, 1B, 1C, 1D, and 1E according to the first through fifth modifications. However, needless to say, the present invention is not limited to the above embodiment and modifications, and can be modified freely without departing from the scope of the invention.

For example, in the embodiment, etc., an air-fuel ratio sensor for detecting the concentration of oxygen contained in exhaust gas (air-fuel ratio) is used as the gas sensor 2. However, the "gas sensor" is not limited to the air-fuel ratio sensor, and may be an oxygen sensor for detecting the concentration (lean/rich) of oxygen, an NOx sensor for detecting the concentration of nitrogen oxide (NOx), or the like. Also, the "gas sensor" may be a sensor for detecting the concentration of a specific gas component (e.g., oxygen) contained in intake gas taken into the combustion chambers of an internal combustion engine.

In embodiment, etc., a temporary current change is produced between the terminals Vs+ and COM of the sensor element section 3 (the electrodes 28 and 22 of the electromotive force cell 24) through use of the constant current −Iconst, which is a temporary current change, and a voltage change amount ΔVs (response change amount) produced as a result of the current change is detected. The circuit configuration of the sensor element section control circuit 40 may be modified so as to produce a temporary voltage change, detect a response change amount of the current produced as a result of the voltage change, and detect the element resistance therefrom.

In the embodiment, etc., the instruction command SC, which is a serial command, is used as an instruction signal. However, the instruction signal may change depending on the circuit configuration of the sensor element section control circuit 40 which constitutes the change amount detection means. The instruction signal may be a digital signal such as a serial signal or a pulse signal, or an analog signal. In the case where the instruction signal is an analog signal, for example, a current signal or a voltage signal which produces the above-mentioned temporary change in current or voltage may be used as an instruction signal.

In the embodiment, the length of all the 1-2 periods $T_{1-2}$, including the pre-output 1-2 period $TB_{1-2}$, is restricted to the maximum value $TB_{1-2max}$ or less. However, only the length of the pre-output 1-2 period $TB_{1-2}$ may be restricted by separately performing timing adjustment control.

In the embodiment, the length of all the 1-2 periods $T_{1-2}$, including the pre-output 1-2 period $TB_{1-2}$, is restricted to the minimum value $TB_{1-2min}$ or greater. However, only the length of the pre-output 1-2 period $TB_{1-2}$ may be restricted by separately performing timing adjustment control.

In the embodiment, the value of the ΔVs detection timing counter is increased by 1 (increment) by the trailing edge interruption processing (see FIG. 5) on the basis of the trailing edge PSD of each PWM pulse PS (step S32). However, separately from the trailing edge interruption processing, the processing corresponding to step S32; i.e., the processing of increasing the value of the ΔVs detection timing counter by 1 (increment) may be performed on the basis of the leading edge PSU of each PWM pulse PS. Alternatively, the processing corresponding to step S32 may be performed within the heater energization control routine (see FIG. 6), for example, after step S77.

Although the first through fifth modifications show five combinations of the various means contained in the prevention means, the combination of the various means is not limited thereto.

For example, the period postponing output means may be omitted from the gas sensor control apparatus of the first modification. In such a case, the gas sensor control apparatus merely stops the output of the instruction command SC when the CAN transmission is being performed.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-030966 filed Feb. 15, 2012, Japanese Patent Application No. 2012-039668 filed Feb. 27, 2012 and Japanese Patent Application No. 2012-185892 filed Aug. 24, 2012, the above-identified applications incorporated herein by reference in their entirety.

What is claimed is:

1. A gas sensor control apparatus for controlling a gas sensor which includes a sensor element section made of a solid electrolyte member and detecting the concentration of a gas, and a heater section for heating the sensor element section, comprising:
   change amount detection means for causing a temporary change in voltage between electrodes of the sensor element section or current flowing between the electrodes and for detecting, as a response change amount, a change in the voltage or the current produced in response to the temporary change;
   element resistance detection means for detecting an element resistance of the sensor element section on the basis of the response change amount;
   instruction signal output means for outputting an instruction signal for instructing the change amount detection means to detect the response change amount; and
   heater energization control means for on-off controlling the state of supply of electric current to the heater section through use of pulses having a fixed period, wherein
   when, of an energization ON edge timing of the respective pulses at which the state of supply of electric current to the heater section is switched from an OFF state to an ON state and an energization OFF edge timing of the respective pulses at which the state of supply of electric current to the heater section is switched from the ON state to the OFF state, a timing which occurs at fixed intervals corresponding to the fixed period is defined as a first timing, and a timing which changes depending on a pulse width of the pulses is defined as a second timing, the instruction signal output means outputs the instruction signal at a third timing which comes after elapse of a predetermined wait time from the second timing.

2. The gas sensor control apparatus according to claim 1, wherein the heater energization control means feedback-controls the supply of electric current to the heater section such that the element resistance detected by the element resistance detection means becomes equal to a target resistance.

3. The gas sensor control apparatus according to claim 1, wherein the instruction signal output means outputs the instruction signal every n-th period, where n is an integer equal to or greater than 2.

4. The gas sensor control apparatus according to claim 1, wherein
   a time between a commencement of the output of the instruction signal and a completion of the detection of the response change amount by the change amount detection means is defined as a detection delay time;
   periods each continuing from the first timing to the second timing which comes next are defined as 1-2 periods;
   periods each continuing from the second timing to the first timing which comes next are defined as 2-1 periods;
   of the 2-1 periods, those which include the third timing at which the instruction signal is output are defined as an output 2-1 period;
   of the 1-2 periods, those immediately before the output 2-1 period are defined as a pre-output 1-2 period; and
   the heater energization control means includes maximum value restriction means for restricting the length of the pre-output 1-2 period to a maximum value or less which is previously determined within a range within which the output 2-1 period become longer than the sum of the wait time and the detection delay time.

5. The gas sensor control apparatus according to claim 4, wherein the maximum value restriction means restricts the length of all the 1-2 periods $T_{1\text{-}2}$, including the pre-output 1-2 period, to the maximum value or less.

6. The gas sensor control apparatus according to claim 4, wherein the heater energization control means includes minimum value restriction means for restricting the length of the pre-output 1-2 period to a predetermined minimum value or greater, where the minimum value is greater than zero.

7. The gas sensor control apparatus according to claim 6, wherein the minimum value restriction means restricts the length of all the 1-2 periods, including the pre-output 1-2 period, to the minimum value or greater.

8. The gas sensor control apparatus according to claim 6, wherein the first timing is the energization ON edge timing, and the second timing is the energization OFF edge timing.

9. The gas sensor control apparatus according to claim 1, further comprising:
   data transmission means for transmitting data to an external device; and
   prevention means for preventing use of the response change amount and the element resistance obtained therefrom, the response change amount being affected by the transmission of data due to overlap between the transmission period of the data and at least a portion of the detection period of the response change amount subsequent to the output of the instruction signal at the third timing.

10. The gas sensor control apparatus according to claim 9, wherein the prevention means includes:
   pre-output transmission determination means for determining, prior to the output of the instruction signal at the third timing, whether or not the transmission of the data by the data transmission means is being performed at a pre-output determination timing within the period to which the third timing belongs, the pre-output determination timing coming before the third timing; and
   output stopping means for stopping the output of the instruction signal at the third timing when the transmission of the data is determined to be being performed.

11. The gas sensor control apparatus according to claim 10, wherein
   the instruction signal output means outputs the instruction signal every n-th period, where n is an integer equal to or greater than 2; and
   the prevention means includes period postponing output means, operable when the output of the instruction signal at the third timing is stopped, for outputting the instruction signal at the third timing in a period subsequent to the period in which the output of the instruction signal was stopped.

12. The gas sensor control apparatus according to claim 10, wherein
   the instruction signal output means outputs the instruction signal every n-th period, where n is an integer equal to or greater than 2; and
   the prevention means includes timing postponing output means, operable when the output of the instruction signal at the third timing is stopped, for outputting the instruction signal at a fourth timing within the period in which the output of the instruction signal was stopped, the fourth timing coming after the third timing.

13. The gas sensor control apparatus according to claim 9, wherein the prevention means includes:
   intra-period transmission determination means for determining, at the first timing within the period to which the third timing belongs, whether or not the transmission of the data by the data transmission means is performed within the period; and
   output stopping means for stopping the output of the instruction signal at the third timing when the transmission of the data is determined to be performed.

14. The gas sensor control apparatus according to claim 9, wherein the prevention means includes:
   pre-detection transmission determination means for determining whether or not the transmission of the data by the data transmission means is being performed at a pre-detection determination timing within the period to which the third timing belongs, the pre-detection determination timing coming before the detection period; and
   use prohibition means for preventing use of the response change amount detected in the detection period or the element resistance detected from the response change amount when the transmission of the data is determined to be being performed.

15. The gas sensor control apparatus according to claim 14, wherein
   the instruction signal output means outputs the instruction signal every n-th period, where n is an integer equal to or greater than 2; and
   the prevention means includes re-output means, operable when the pre-detection transmission determination means determines that the transmission of the data is being performed, for causing the instruction signal output means to output the instruction signal again in a period subsequent to the period in which the instruction signal was output.

16. The gas sensor control apparatus according to claim 9, wherein the prevention means includes:
   overlap determination means for determining whether or not at least a portion of the detection period has actually overlapped with the transmission period of transmission of the data transmitted by the data transmission means; and
   use prohibition means for preventing use of the response change amount detected in the detection period or the element resistance detected from the response change amount when at least a portion of the detection period is determined to have overlapped with the transmission period.

17. The gas sensor control apparatus according to claim 16, wherein
   the instruction signal output means outputs the instruction signal every n-th period, where n is an integer equal to or greater than 2; and
   the prevention means includes re-output means, operable when the overlap determination means determines that at least a portion of the detection period has overlapped with the transmission period, for causing the instruction signal output means to output the instruction signal again in a period subsequent to the period in which the instruction signal was output.

* * * * *